United States Patent
Shelton et al.

(10) Patent No.: US 12,414,820 B2
(45) Date of Patent: *Sep. 16, 2025

(54) ENDOSCOPE UNCLOGGING SYSTEM AND METHOD

(71) Applicant: GYRUS ACMI, INC., Westborough, MA (US)

(72) Inventors: Kurt G. Shelton, Bedford, MA (US); Michaella C. Wright, Southborough, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/611,831

(22) Filed: Mar. 21, 2024

(65) Prior Publication Data

US 2024/0261026 A1     Aug. 8, 2024

Related U.S. Application Data

(63) Continuation of application No. 16/803,612, filed on Feb. 27, 2020, now Pat. No. 12,016,626, which is a
(Continued)

(51) Int. Cl.
*A61B 1/015*     (2006.01)
*A61B 1/00*     (2006.01)
(Continued)

(52) U.S. Cl.
CPC .......... *A61B 18/26* (2013.01); *A61B 1/00006* (2013.01); *A61B 1/00055* (2013.01);
(Continued)

(58) Field of Classification Search
CPC . A61B 1/00006; A61B 1/00094; A61B 1/015; A61B 1/121; A61B 1/126;
(Continued)

(56) References Cited

U.S. PATENT DOCUMENTS

| | | | |
|---|---|---|---|
| 4,971,034 A | | 11/1990 | Doi et al. |
| 5,047,012 A | * | 9/1991 | Leuschner ............ A61M 1/772 604/152 |

(Continued)

FOREIGN PATENT DOCUMENTS

| | | |
|---|---|---|
| AU | 2019217992 | 9/2024 |
| CA | 2734120 C | 9/2016 |

(Continued)

OTHER PUBLICATIONS

"U.S. Appl. No. 16/803,612, Advisory Action mailed Oct. 5, 2023", 3 pgs.

(Continued)

*Primary Examiner* — Michael J Carey
*Assistant Examiner* — Stephen Floyd London
(74) *Attorney, Agent, or Firm* — Schwegman Lundberg & Woessner, P.A.

(57) ABSTRACT

Systems and methods of in situ unclogging a working channel in a medical device during a procedure are disclosed. An exemplary unclogging system comprises a flow sensor to sense a flow rate through a working channel, and a control module to detect a channel state indicating a presence or absence of clogging based on the flow rate. In the presence of channel clogging, the control module can control one or more of an irrigation source or a suction source to provide respectively irrigation fluid or suction pressure to unclog the obstructed channel. The control module can adjust one or more of an irrigation flow rate or a suction flow rate through the working channel to maintain a desired pressure of the anatomical environment at the anatomical site, or to maintain a desired flow condition in the working channel, during the procedure.

20 Claims, 14 Drawing Sheets

Related U.S. Application Data continuation-in-part of application No. PCT/US2019/017391, filed on Feb. 9, 2019.

(60) Provisional application No. 62/628,513, filed on Feb. 9, 2018.

(51) Int. Cl.

| | | |
|---|---|---|
| *A61B 1/018* | (2006.01) | |
| *A61B 1/05* | (2006.01) | |
| *A61B 1/06* | (2006.01) | |
| *A61B 1/12* | (2006.01) | |
| *A61B 1/307* | (2006.01) | |
| *A61B 1/31* | (2006.01) | |
| *A61B 17/3207* | (2006.01) | |
| *A61B 18/24* | (2006.01) | |
| *A61B 18/26* | (2006.01) | |
| *A61M 1/00* | (2006.01) | |
| *H01S 3/067* | (2006.01) | |
| *A61B 18/00* | (2006.01) | |
| *H01S 3/16* | (2006.01) | |

(52) U.S. Cl.
CPC .......... *A61B 1/00087* (2013.01); *A61B 1/015* (2013.01); *A61B 1/018* (2013.01); *A61B 1/06* (2013.01); *A61B 1/126* (2013.01); *A61B 1/307* (2013.01); *A61B 1/31* (2013.01); *A61B 18/24* (2013.01); *A61M 1/74* (2021.05); *A61M 1/77* (2021.05); *H01S 3/06716* (2013.01); *A61B 1/00045* (2013.01); *A61B 1/00105* (2013.01); *A61B 1/05* (2013.01); *A61B 17/320783* (2013.01); *A61B 2018/00482* (2013.01); *A61B 2018/00505* (2013.01); *A61B 2018/00511* (2013.01); *A61B 2018/00559* (2013.01); *A61B 2018/00642* (2013.01); *A61B 2018/00672* (2013.01); *A61B 2018/00678* (2013.01); *A61B 2018/00696* (2013.01); *A61B 2018/00702* (2013.01); *A61B 2018/00773* (2013.01); *A61B 2018/00982* (2013.01); *A61B 2217/005* (2013.01); *A61B 2217/007* (2013.01); *A61B 2562/0247* (2013.01); *A61M 2205/3334* (2013.01); *A61M 2205/3344* (2013.01); *H01S 3/1616* (2013.01)

(58) Field of Classification Search
CPC .......... A61B 1/303; A61B 2017/32008; A61B 2217/005; A61B 2217/007; A61B 1/00039; A61B 1/0004; A61B 1/00042; A61M 1/77; A61M 1/772; A61M 1/777; A61M 3/0216; A61M 3/022; A61M 2205/3334; A61M 2205/3341
See application file for complete search history.

(56) References Cited

U.S. PATENT DOCUMENTS

| | | |
|---|---|---|
| 5,830,176 A | 11/1998 | Mackool |
| 6,156,049 A | 12/2000 | Lovato et al. |
| 8,109,872 B2 | 2/2012 | Kennedy, II et al. |
| 9,259,231 B2 | 2/2016 | Navve et al. |
| 9,308,315 B2 | 4/2016 | Stubkjaer et al. |
| 9,907,563 B2 | 3/2018 | Germain et al. |
| 12,016,626 B2 | 6/2024 | Shelton et al. |
| 12,023,096 B2 | 7/2024 | Shelton et al. |
| 2005/0209561 A1 | 9/2005 | Gordon et al. |
| 2005/0222535 A1 | 10/2005 | Uesugi et al. |
| 2006/0047185 A1 | 3/2006 | Shener et al. |
| 2006/0264995 A1 | 11/2006 | Fanton et al. |
| 2007/0244363 A1* | 10/2007 | Sano .................. A61M 13/003 600/118 |
| 2007/0260111 A1* | 11/2007 | Baur .................. A61M 3/0202 600/101 |
| 2008/0154185 A1 | 6/2008 | Blight |
| 2009/0058996 A1 | 3/2009 | Mitsuhashi |
| 2010/0004510 A1 | 1/2010 | Kuroshima |
| 2010/0049119 A1 | 2/2010 | Norman et al. |
| 2010/0076304 A1 | 3/2010 | Teramura |
| 2011/0082449 A1 | 4/2011 | Melsky et al. |
| 2011/0237880 A1 | 9/2011 | Hamel et al. |
| 2012/0116168 A1 | 5/2012 | Moellstam et al. |
| 2013/0303852 A1 | 11/2013 | Hiraga et al. |
| 2014/0323953 A1 | 10/2014 | Sorensen et al. |
| 2015/0119645 A1 | 4/2015 | Baldwin |
| 2015/0216394 A1 | 8/2015 | Toyoda |
| 2015/0320303 A1 | 11/2015 | Kawase |
| 2015/0342682 A1 | 12/2015 | Bowe |
| 2016/0022126 A1 | 1/2016 | Ramesh et al. |
| 2016/0022289 A1 | 1/2016 | Wan |
| 2016/0135894 A1 | 5/2016 | Finkman et al. |
| 2016/0157954 A1 | 6/2016 | Sagon et al. |
| 2016/0206805 A1* | 7/2016 | Hassidov .............. A61M 3/022 |
| 2017/0173256 A1* | 6/2017 | Hassidov .............. A61M 1/772 |
| 2017/0220754 A1* | 8/2017 | Harrah .................. A61B 18/26 |
| 2018/0070981 A1* | 3/2018 | Govari .................. A61B 17/24 |
| 2018/0084980 A1 | 3/2018 | Watanabe et al. |
| 2018/0168439 A1 | 6/2018 | Hibbs et al. |
| 2018/0289394 A1 | 10/2018 | Shah |
| 2018/0361055 A1* | 12/2018 | Pereira .................. A61M 1/72 |
| 2019/0008545 A1 | 1/2019 | Stulen et al. |
| 2019/0134279 A1 | 5/2019 | Benamou et al. |
| 2019/0247566 A1 | 8/2019 | Hassidov et al. |
| 2019/0262532 A1* | 8/2019 | Oh ........................ A61M 3/022 |
| 2019/0282073 A1 | 9/2019 | Truckai |
| 2020/0187761 A1 | 6/2020 | Shelton |
| 2020/0187768 A1 | 6/2020 | Shelton et al. |
| 2020/0405130 A9 | 12/2020 | Shelton |
| 2021/0045811 A1 | 2/2021 | Shelton et al. |
| 2021/0220529 A1 | 7/2021 | Wang |
| 2021/0236728 A1 | 8/2021 | Fanning et al. |
| 2021/0244267 A1 | 8/2021 | Shtul et al. |
| 2024/0252245 A1 | 8/2024 | Shelton et al. |

FOREIGN PATENT DOCUMENTS

| | | |
|---|---|---|
| CN | 104640523 | 5/2015 |
| CN | 104661624 | 5/2015 |
| CN | 111683580 A | 9/2020 |
| CN | 115175626 A | 10/2022 |
| CN | 115334982 A | 11/2022 |
| CN | 119606285 | 3/2025 |
| DE | 112021001260 T5 | 12/2022 |
| DE | 112021001396 T5 | 12/2022 |
| EP | 0048410 A1 | 3/1982 |
| EP | 1086674 A1 | 3/2001 |
| EP | 3429453 A1 | 1/2019 |
| EP | 3749167 | 11/2024 |
| JP | S5971736 A | 4/1984 |
| JP | H03207371 A | 9/1991 |
| JP | H08201026 A | 8/1996 |
| JP | 2003210485 A | 7/2003 |
| JP | 2007244679 A | 9/2007 |
| JP | 2009506817 A | 2/2009 |
| JP | 2010075314 A | 4/2010 |
| JP | 2016043178 A | 4/2016 |
| JP | 2016515441 A | 5/2016 |
| JP | 2016533830 A | 11/2016 |
| JP | 2017500172 A | 1/2017 |
| JP | 2017080348 A | 5/2017 |
| JP | 2019093138 A | 6/2019 |
| JP | 7460526 B2 | 4/2024 |
| JP | 7498287 | 6/2024 |
| JP | 7524336 | 7/2024 |
| WO | WO-2011032165 A2 | 3/2011 |
| WO | WO-2013099507 A1 | 7/2013 |
| WO | WO-2015029039 A1 | 3/2015 |
| WO | WO-2015069387 A1 | 5/2015 |
| WO | WO-2019157247 A1 | 8/2019 |

(56) References Cited

FOREIGN PATENT DOCUMENTS

| WO | WO-2019157247 A9 | 4/2020 |
|---|---|---|
| WO | WO-2021173775 A1 | 9/2021 |
| WO | WO-2021173791 A1 | 9/2021 |

OTHER PUBLICATIONS

"U.S. Appl. No. 16/803,612, Advisory Action mailed Dec. 1, 2022", 3 pgs.
"U.S. Appl. No. 16/803,612, Corrected Notice of Allowability mailed Feb. 28, 2024", 6 pgs.
"U.S. Appl. No. 16/803,612, Corrected Notice of Allowability mailed Apr. 23, 2024", 7 pgs.
"U.S. Appl. No. 16/803,612, Examiner Interview Summary mailed Feb. 8, 2024", 3 pgs.
"U.S. Appl. No. 16/803,612, Examiner Interview Summary mailed Mar. 28, 2023", 3 pgs.
"U.S. Appl. No. 16/803,612, Examiner Interview Summary mailed Jun. 3, 2022", 3 pgs.
"U.S. Appl. No. 16/803,612, Examiner Interview Summary mailed Nov. 8, 2022", 3 pgs.
"U.S. Appl. No. 16/803,612, Final Office Action mailed Jul. 24, 2023", 35 pgs.
"U.S. Appl. No. 16/803,612, Final Office Action mailed Sep. 14, 2022", 34 pgs.
"U.S. Appl. No. 16/803,612, Non Final Office Action mailed Mar. 7, 2022", 38 pgs.
"U.S. Appl. No. 16/803,612, Non Final Office Action mailed Nov. 8, 2023", 26 pgs.
"U.S. Appl. No. 16/803,612, Non Final Office Action mailed Dec. 28, 2022", 32 pgs.
"U.S. Appl. No. 16/803,612, Notice of Allowance mailed Feb. 14, 2024", 9 pgs.
"U.S. Appl. No. 16/803,612, Response filed Feb. 5, 2024 to Non Final Office Action mailed Nov. 8, 2023", 15 pgs.
"U.S. Appl. No. 16/803,612, Response filed Mar. 23, 2023 to Non Final Office Action mailed Dec. 28, 2022", 14 pgs.
"U.S. Appl. No. 16/803,612, Response filed May 31, 2022 to Non Final Office Action mailed Mar. 7, 2022", 25 pgs.
"U.S. Appl. No. 16/803,612, Response filed Sep. 25, 2023 to Final Office Action mailed Jul. 24, 2023", 15 pgs.
"U.S. Appl. No. 16/803,612, Response filed Oct. 24, 2023 to Advisory Action mailed Oct. 5, 2023", 14 pgs.
"U.S. Appl. No. 16/803,612, Response filed Nov. 8, 2022 to Final Office Action mailed Sep. 14, 2022", 18 pgs.
"U.S. Appl. No. 16/803,612, Response filed Dec. 9, 2022 to Advisory Action mailed Dec. 1, 2022", 17 pgs.
"U.S. Appl. No. 16/803,649, Advisory Action mailed Feb. 13, 2024", 3 pgs.
"U.S. Appl. No. 16/803,649, Advisory Action mailed Mar. 24, 2023", 5 pgs.
"U.S. Appl. No. 16/803,649, Examiner Interview Summary mailed Feb. 6, 2024", 3 pgs.
"U.S. Appl. No. 16/803,649, Examiner Interview Summary mailed Feb. 21, 2023", 2 pgs.
"U.S. Appl. No. 16/803,649, Examiner Interview Summary mailed Oct. 5, 2022", 3 pgs.
"U.S. Appl. No. 16/803,649, Final Office Action mailed Dec. 13, 2023", 24 pgs.
"U.S. Appl. No. 16/803,649, Final Office Action mailed Dec. 22, 2022", 17 pgs.
"U.S. Appl. No. 16/803,649, Non Final Office Action mailed May 26, 2023", 22 pgs.
"U.S. Appl. No. 16/803,649, Non Final Office Action mailed Jun. 5, 2024", 25 pgs.
"U.S. Appl. No. 16/803,649, Non Final Office Action mailed Jul. 7, 2022", 15 pgs.
"U.S. Appl. No. 16/803,649, Response filed Feb. 21, 2023 to Final Office Action mailed Dec. 22, 2022", 12 pgs.
"U.S. Appl. No. 16/803,649, Response filed Apr. 14, 2022 to Restriction Requirement mailed Feb. 16, 2022", 8 pgs.
"U.S. Appl. No. 16/803,649, Response filed Aug. 28, 2023 to Non Final Office Action mailed May 26, 2023", 13 pgs.
"U.S. Appl. No. 16/803,649, Response filed Oct. 4, 2022 to Non Final Office Action mailed Jul. 7, 2022", 15 pgs.
"U.S. Appl. No. 16/803,649, Response filed Feb. 2, 2024 to Final Office Action mailed Dec. 13, 2023", 13 pgs.
"U.S. Appl. No. 16/803,649, Restriction Requirement mailed Feb. 16, 2022", 6 pgs.
"U.S. Appl. No. 16/968,800, Corrected Notice of Allowability mailed Jun. 3, 2024", 2 pgs.
"U.S. Appl. No. 16/968,800, Examiner Interview Summary mailed Jan. 31, 2024", 3 pgs.
"U.S. Appl. No. 16/968,800, Final Office Action mailed Nov. 30, 2023", 13 pgs.
"U.S. Appl. No. 16/968,800, Non Final Office Action mailed Jun. 21, 2023", 13 pgs.
"U.S. Appl. No. 16/968,800, Notice of Allowance mailed Feb. 14, 2024", 8 pgs.
"U.S. Appl. No. 16/968,800, Response filed Jan. 25, 2024 to Final Office Action mailed Nov. 30, 2023", 12 pgs.
"U.S. Appl. No. 16/968,800, Response filed May 23, 2023 to Restriction Requirement mailed Apr. 5, 2023", 8 pgs.
"U.S. Appl. No. 16/968,800, Response filed Sep. 21, 2023 to Non Final Office Action mailed Jun. 21, 2023", 13 pgs.
"U.S. Appl. No. 16/968,800, Restriction Requirement mailed Apr. 5, 2023", 5 pgs.
"Australian Application Serial No. 2019217992, First Examination Report mailed Nov. 22, 2023", 4 pgs.
"Australian Application Serial No. 2019217992, Response filed Mar. 26, 2024 to First Examination Report mailed Nov. 22, 2023", 21 pgs.
"Australian Application Serial No. 2019217992, Response filed May 24, 2024 to Subsequent Examiners Report mailed Apr. 8, 2024", 17 pgs.
"Australian Application Serial No. 2019217992, Subsequent Examiners Report mailed Apr. 8, 2024", 2 pgs.
"Canadian Application Serial No. 3,169,535, Examiners Rule 86(2) Requisition mailed Sep. 29, 2023", 4 pgs.
"Canadian Application Serial No. 3,169,535, Response filed Jan. 25, 2024 to Examiners Rule 86(2) Requisition mailed Sep. 29, 2023", 16 pgs.
"Canadian Application Serial No. 3,169,549, Examiners Rule 86(2) Report mailed Sep. 29, 2023", 4 pgs.
"Canadian Application Serial No. 3,169,549, Response filed Jan. 29, 2024 to Examiners Rule 86(2) Report mailed Sep. 29, 2023", 19 pgs.
"Chinese Application Serial No. 201980012086.0, First Office Action mailed Jan. 15, 2024", with English translation, 21 pgs.
"Chinese Application Serial No. 201980012086.0, Response filed May 8, 2024 to Office Action mailed Jan. 15, 2024", w/ English Claims, 11 pgs.
"European Application Serial No. 19750915.1, Extended European Search Report mailed Nov. 22, 2021", 8 pgs.
"European Application Serial No. 19750915.1, Response filed Mar. 16, 2021", 9 pgs.
"European Application Serial No. 19750915.1, Response filed Jun. 9, 2022 to Extended European Search Report mailed Nov. 22, 2021", 10 pgs.
"Indian Application Serial No. 202247046058, First Examination Report mailed Apr. 11, 2023", 6 pgs.
"Indian Application Serial No. 202247046058, Response filed Oct. 4, 2023 to Office Action mailed Apr. 11, 2023", 24 pgs.
"International Application Serial No. PCT/US2019/017153, International Search Report mailed Apr. 30, 2019", 2 pgs.
"International Application Serial No. PCT/US2019/017153, Written Opinion mailed Apr. 30, 2019", 6 pgs.
"International Application Serial No. PCT/US2021/019568, International Preliminary Report on Patentability mailed Sep. 9, 2022", 7 pgs.
"International Application Serial No. PCT/US2021/019568, International Search Report mailed May 14, 2021", 4 pgs.

(56) References Cited

OTHER PUBLICATIONS

"International Application Serial No. PCT/US2021/019568, Written Opinion mailed May 14, 2021", 5 pgs.
"International Application Serial No. PCT/US2021/019599, International Preliminary Report on Patentability mailed Sep. 9, 2022", 7 pgs.
"International Application Serial No. PCT/US2021/019599, International Search Report mailed May 19, 2021", 5 pgs.
"International Application Serial No. PCT/US2021/019599, Written Opinion mailed May 19, 2021", 5 pgs.
"Japanese Application Serial No. 2020-542995, Notification of Reasons for Refusal mailed May 22, 2023", w/ English translation, 8 pgs.
"Japanese Application Serial No. 2020-542995, Notification of Reasons for Rejection mailed Nov. 7, 2022", w/ English Translation, 9 pgs.
"Japanese Application Serial No. 2020-542995, Response filed Feb. 3, 2023 to Notification of Reasons for Rejection mailed Nov. 7, 2022", with English claims, 10 pgs.
"Japanese Application Serial No. 2020-542995, Response filed Sep. 7, 2023 to Notification of Reasons for Refusal mailed May 22, 2023", w/ english claims, 9 pgs.
"Japanese Application Serial No. 2022-551708, Examiners Decision of Final Refusal mailed Jan. 15, 2024", W/English Translation, 6 pgs.
"Japanese Application Serial No. 2022-551708, Notification of Reasons for Refusal mailed Aug. 28, 2023", w/ English Translation, 9 pgs.
"Japanese Application Serial No. 2022-551708, Response filed Mar. 27, 2024 to Examiners Decision of Final Refusal mailed Jan. 15, 2024", w/ english claims, 17 pgs.
"Japanese Application Serial No. 2022-551708, Response filed Oct. 13, 2023 to Notification of Reasons for Refusal mailed Aug. 28, 2023", with English claims, 12 pgs.
"Japanese Application Serial No. 2022-551714, Notification of Reasons for Refusal mailed Oct. 23, 2023", w/ English Translation, 15 pgs.
"Japanese Application Serial No. 2022-551714, Notification of Reasons for Rejection mailed Mar. 4, 2024", W/English Translation, 8 pgs.
"Japanese Application Serial No. 2022-551714, Response filed May 31, 2024 to Notification of Reasons for Rejection mailed Mar. 4, 2024", W/English Claims, 8 pgs.
"Japanese Application Serial No. 2022-551714, Response filed Dec. 18, 2023 to Notification of Reasons for Refusal mailed Oct. 23, 2023", with English claims, 10 pgs.
"Japanese Application Serial No. 2024-045080, Notification of Reasons for Refusal mailed May 27, 2024", w/ English Translation, 13 pgs.
"Japanese Application Serial No. 2024-51659, Voluntary Amendment filed May 17, 2024", with machine translation, 9 pgs.
"Korean Application Serial No. 2020-7025950, Notice of Preliminary Rejection mailed Jan. 30, 2024", with machine translation, 16 pgs.
"Korean Application Serial No. 2020-7025950, Response filed Mar. 28, 2024 to Notice of Preliminary Rejection mailed Jan. 30, 2024", w/ current English claims, 18 pgs.
"Mexican Application Serial No. MX/a/2020/008321, Office Action mailed Apr. 16, 2024", with machine translation, 7 pgs.
"Mexican Application Serial No. MX/a/2020/008321, Response filed Jun. 6, 2024 to Office Action mailed Apr. 16, 2024", with machine translation, 13 pgs.
"U.S. Appl. No. 16/803,649, Response filed Jul. 3, 2024 to Non Final Office Action mailed Jun. 5, 2024", 11 pgs.
"Japanese Application Serial No. 2024-045080, Response filed Sep. 11, 2024 to Notification of Reasons for Refusal mailed May 27, 2024", w current English claims, 12 pgs.
"Canadian Application Serial No. 3,169,549, Examiners Rule 86(2) Report mailed Aug. 26, 2024", 4 pgs.
"Canadian Application Serial No. 3,169,535, Examiners Rule 86(2) Report mailed Aug. 16, 2024", 4 pgs.
"U.S. Appl. No. 16/803,649, Examiner Interview Summary mailed Nov. 29, 2024", 3 pgs.
"U.S. Appl. No. 16/803,649, Final Office Action mailed Oct. 9, 2024", 25 pgs.
"U.S. Appl. No. 16/803,649, Advisory Action mailed Dec. 10, 2024", 3 pgs.
"Japanese Application Serial No. 2024-045080, Examiners Decision of Final Refusal mailed Nov. 18, 2024", w English translation, 7 pgs.
"Canadian Application Serial No. 3,169,535, Response filed Dec. 16, 2024 to Examiners Rule 86(2) Report mailed Aug. 16, 2024", w claims, 13 pgs.
"Canadian Application Serial No. 3,169,549, Response filed Dec. 27, 2024 to Examiners Rule 86(2) Report mailed Aug. 26, 2024", w claims, 25 pgs.
"U.S. Appl. No. 16/803,649, Response filed Nov. 25, 2024 to Final Office Action mailed Oct. 9, 2024", 13 pgs.
"Japanese Application Serial No. 2024-045080, Response filed Feb. 14, 2025 to Examiners Decision of Final Refusal mailed Nov. 18, 2024", w english claims, 13 pgs.
"U.S. Appl. No. 16/ 803,649, Notice of Allowance mailed Mar. 28, 2025", 12 pgs.
"Indian Application Serial No. 202247046058, Hearing Notice mailed Feb. 10, 2025", 2 pgs.
"Indian Application Serial No. 202247046712, First Examination Report mailed Feb. 18, 2025", 6 pgs.
"Chinese Application Serial No. 202180016835.4, Office Action mailed Mar. 18, 2025", w English Translation, 20 pgs.
"European Application Serial No. 24211085.6, Extended European Search Report mailed Apr. 15, 2025", 6 pgs.
"Indian Application Serial No. 202247046058, Response filed Apr. 1, 2025 to Hearing Notice mailed Feb. 10, 2025", w claims, 23 pgs.
"Chinese Application Serial No. 202180017112.6, Office Action mailed Mar. 22, 2025", W English Translation, 27 pgs.
U.S. Appl. No. 16/803,612 U.S. Pat. No. 12,016,626, filed Feb. 27, 2020, Endoscope Unclogging System and Method.
U.S. Appl. No. 16/803,649, filed Feb. 27, 2020, Suction and Irrigation Control System and Method.
U.S. Appl. No. 16/968,800 U.S. Pat. No. 12,023,096, filed Aug. 10, 2020, Medical Laser Apparatus and System.
U.S. Appl. No. 18/634,485, filed Apr. 12, 2024, Medical Laser Apparatus and System.

* cited by examiner

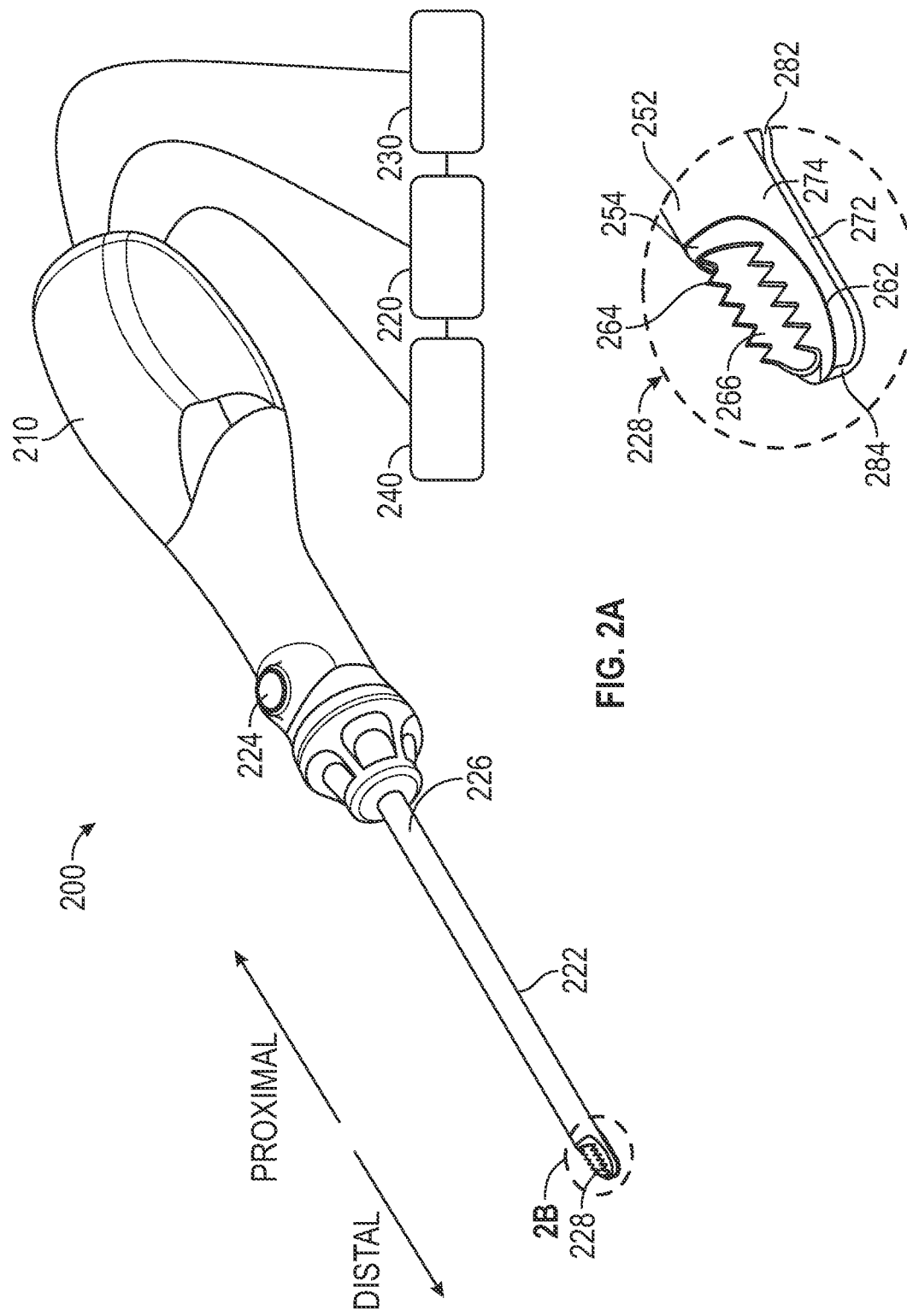

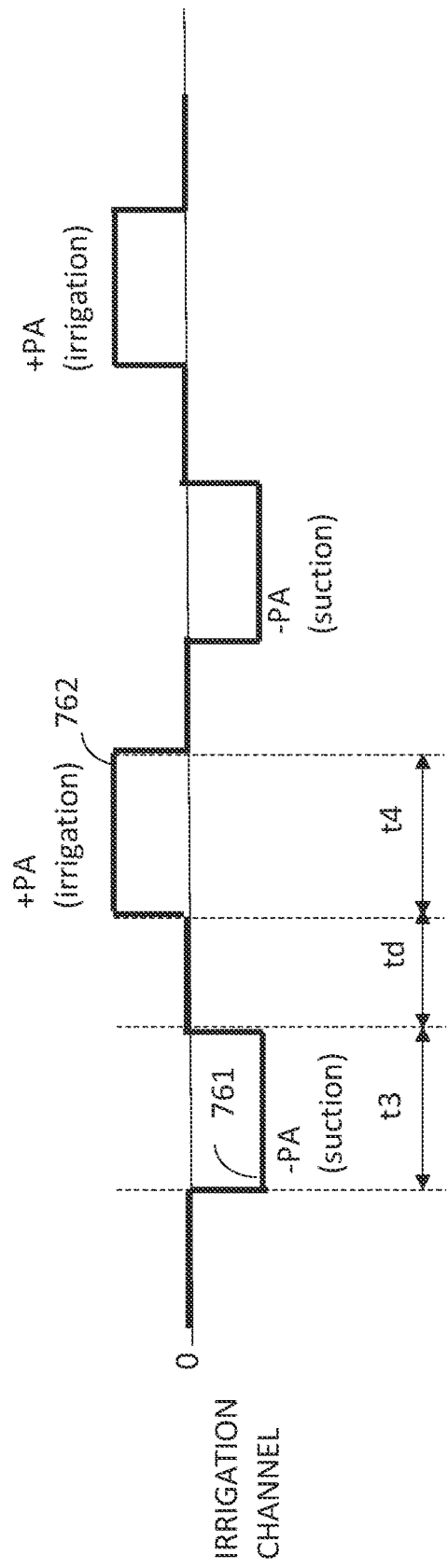
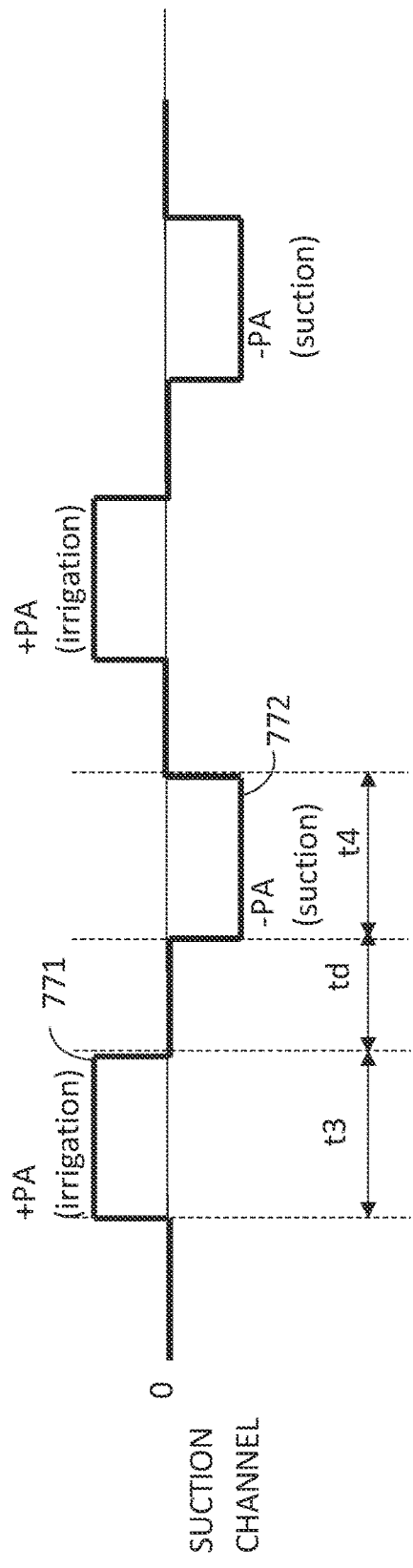

ENDOSCOPE UNCLOGGING SYSTEM AND METHOD

CLAIM OF PRIORITY

This application is a Continuation of U.S. patent application Ser. No. 16/803,612, titled "ENDOSCOPE UNCLOGGING SYSTEM AND METHOD," filed Feb. 27, 2020, which is a Continuation-in-Part and claims benefit of International Patent Application Serial Number PCT/US2019/017391, titled "SYSTEM, METHOD AND COMPUTER-READABLE STORAGE DEVICE FOR CONTROLLING LASER LIGHT SOURCE OF LITHOTRIPSY DEVICE," filed Feb. 8, 2019, which claims the benefit of priority, and incorporates by reference the entirety of U.S. Provisional Application No. 62/628,513 filed on Feb. 9, 2018, the benefit of each of which is hereby presently claimed, and the entirety of each of which is hereby incorporated by reference herein.

CROSS REFERENCE TO RELATED APPLICATION

This application is related to commonly assigned U.S. patent application Ser. No. 16/803,649, entitled "SUCTION AND IRRIGATION CONTROL SYSTEM AND METHOD", filed on Feb. 27, 2020, which is incorporated by reference in their entirety herein.

TECHNICAL FIELD

This document relates generally to an endoscopy system, and more specifically relates to an unclogging system for unclogging an endoscope while keeping the in situ pressure of an anatomical environment at the anatomical site under control during an endoscopic procedure.

BACKGROUND

Endoscopes are typically used to provide access to an internal location of a patient so that a doctor is provided with visual access. Some endoscopes are used in minimally invasive surgery to remove unwanted tissue or foreign objects from the body of the patient. For example, an endoscopic tissue removal device is an instrument used by a clinician to remotely access necrotic, cancerous, damaged, infected or otherwise unwanted soft tissue, bone, or other anatomical structures at an anatomical site, excise said unwanted matters from the adjacent anatomy, and transport them away from the anatomical site. A nephroscope is used by a clinician to inspect the renal system, and to perform various procedures under direct visual control. For example, percutaneous nephrolithotomy (PCNL) is procure involving placement of a nephroscope through the patient's flank into the renal pelvis. Calculi or mass from various regions of a body including, for example, urinary system, gallbladder, nasal passages, gastrointestinal tract, stomach, or tonsils, can be visualized and extracted. Calculi of larger sizes can be ablated into smaller fragments using oscillating forces such as shock waves, ultrasonic energy (via a specialized device such as an ultrasonic lithotripter), or lasers.

Some endoscopes have suction channels (also known as aspiration channels) to transport resected tissue, calculi (e.g., stones or stone fragments in various stone-forming regions) and mass, among other unwanted matters. A flow of irrigation agent (e.g., saline solution) can be introduced to the anatomical site through an irrigation channel in the endoscope during the procedure. The irrigation fluid can facilitate removal of the tissue debris, stone fragments, and other unwanted matters through the suction channel. The irrigation fluid can also help maintain a clear visibility of the anatomical environment for the clinician performing the procedure. Additionally, the irrigation flow has a cooling effect on the endoscopic tissue removal device, and can help dissipate the heat generated during ablation of calculi (e.g., kidney stones).

Unwanted matters produced during an endoscopic procedure may accumulate and clog a working channel (e.g., a suction channel or an irrigation channel) of the scope. Monitoring channels for clogging, and timely and efficiently unclogging the obstructed channel can reduce procedure time and improve efficiency, safety, and success of endoscopic procedures.

SUMMARY

The present document describes systems and methods for in situ unclogging of a working channel of an endoscope during an endoscopic procedure, while keeping the pressure at an anatomical site under control during an endoscopic procedure. According to one aspect of the present document, an unclogging system comprises a flow sensor configured to sense a flow rate through a working channel of an endoscope, and a control module configured to detect a channel state indicating a presence or an absence of clogging in the working channel using the sensed flow rate. In response to the presence of clogging in the working channel, the control module can control one or more of an irrigation source or a suction source to provide respectively irrigation fluid or suction pressure to the working channel to unclog the working channel. The control module can automatically adjust one or more of an irrigation flow rate or a suction flow rate through the working channel to maintain the pressure of an anatomical environment at the anatomical site at substantially a desired pressure level (e.g., a predetermined or a user-specified pressure level), or to achieve a desired flow condition that corresponds to the desired pressure, during endoscopic procedure. The irrigation fluid or the suction pressure can be applied for as long as the channel clogging remains present.

Example 1 is a system for unclogging at least one working channel of a medical device during a procedure in a patient. The system comprises: a flow sensor configured to sense a flow rate through the at least one working channel of the medical device; and a control module configured to: detect a channel state using the sensed flow rate, the channel state indicating a presence or an absence of clogging in the at least one working channel; and in response to the detected channel state indicating a presence of clogging in the at least one working channel, control one or more of an irrigation source or a suction source to provide respectively an irrigation fluid or a suction pressure to unclog the at least one working channel.

In Example 2, the subject matter of Example 1 optionally includes the control module that can be configured to control one or more of the irrigation source or the suction source to provide respectively the irrigation fluid or the suction pressure to unclog the at least one working channel for as long as the detected channel state indicating a presence of clogging in the at least one working channel.

In Example 3, the subject matter of any one of Examples 1-2 optionally include or the control module that can be configured to: detect a presence of clogging in the at least one working channel in response to a decrease in the sensed flow rate below a first threshold; and detect an absence of clogging in the at least one working channel in response to an increase in the sensed flow rate above a second threshold.

In Example 4, the subject matter of any one or more of Examples 1-3 optionally includes the control module that can be configured to unclog the at least one working channel including alternating between an application of irrigation fluid and an application of suction pressure to the at least one working channel.

In Example 5, the subject matter of any one or more of Examples 1-4 optionally includes the control module that can be configured to control one or more of the irrigation source or the suction source by adjusting respectively a flow rate of the irrigation fluid or a flow rate of the suction pressure to unclog the at least one working channel.

In Example 6, the subject matter of any one or more of Examples 3-5 optionally includes: a user input configured to receive from a user a desired pressure to be applied to an anatomical environment at an anatomical site in the patient; and a pressure sensor configured to sense a pressure of the anatomical environment at the anatomical site; and wherein the control module is configured to adjust one or more of an irrigation flow rate or a suction flow rate through the at least one working channel to maintain the sensed pressure at substantially a level of the desired pressure.

In Example 7, the subject matter of Example 6 optionally includes: the user input that is configured to receive a desired flow condition in the at least one working channel, the desired flow condition corresponding to the desired pressure to be applied to the anatomical environment; and the control module that is configured to control one or more of an irrigation flow rate or a suction flow rate through at least one working channel of the medical device to maintain the desired flow condition.

In Example 8, the subject matter of any one or more of Examples 6-7 optionally includes the at least one working channel that can include a suction channel and an irrigation channel, and the control module that can be configured to: fluidly couple an irrigation source to one of the irrigation channel or the suction channel to provide an irrigation fluid thereto at an adjustable irrigation flow rate; and fluidly couple a suction source to the other of the irrigation channel or the suction channel to supply a suction pressure thereto at an adjustable suction flow rate.

In Example 9, the subject matter of Example 8 optionally includes the control module that can be configured to: in response to a presence of clogging in the suction channel, control the irrigation source to provide an irrigation fluid to the suction channel; in response to an increase in the sensed pressure of the anatomical environment at the anatomical site, control the suction source to apply a suction pressure to the irrigation channel to maintain the sensed pressure at substantially a level of the desired pressure; and in response to an absence of clogging in the suction channel, control the suction source to apply a suction pressure to the suction channel, and control the irrigation source to provide an irrigation fluid to the irrigation channel.

In Example 10, the subject matter of Example 8 optionally includes the control module that can be configured to: in response to a presence of clogging in the irrigation channel, control the suction source to apply a suction pressure to the irrigation channel; in response to a decrease in the sensed pressure of the anatomical environment at the anatomical site, control the irrigation source to provide an irrigation fluid to the suction channel to maintain the sensed pressure at substantially a level of the desired pressure; and in response to an absence of clogging in the irrigation channel, control the suction source to apply a suction pressure to the suction channel, and control the irrigation source to provide an irrigation fluid to the irrigation channel.

In Example 11, the subject matter of Example 9 optionally includes the desired pressure which can be a substantially net-zero pressure, and wherein the control module can be configured to, in response to the increase in the sensed pressure, control the suction source to apply a suction pressure to the irrigation channel at a level that substantially neutralizes the increase in the sensed pressure.

In Example 12, the subject matter of Example 10 optionally includes the desired pressure which can be a substantially net-zero pressure, and wherein the control module can be configured to, in response to the decrease in the sensed pressure, control the irrigation source to provide an irrigation fluid to the suction channel at an irrigation flow rate that substantially neutralizes the decrease in the sensed pressure.

In Example 13, the subject matter of Example 9 optionally includes the desired pressure which can be a positive pressure, and wherein the control module can be configured to, in response to the increase in the sensed pressure, control the suction source to apply a suction pressure to the irrigation channel at a level to maintain the sensed pressure at substantially a level of the desired positive pressure.

In Example 14, the subject matter of Example 10 optionally includes the desired pressure which can be a positive pressure, and wherein the control module can be configured to, in response to the decrease in the sensed pressure, control the irrigation source to provide an irrigation fluid to the suction channel at an irrigation flow rate such that the sensed pressure is maintained at substantially a level of the desired positive pressure.

In Example 15, the subject matter of Example 9 optionally includes the desired pressure which can be a negative pressure, and wherein the control module can be configured to, in response to the increase in the sensed pressure, control the suction source to apply a suction pressure to the irrigation channel at a level to maintain the sensed pressure at substantially a level of the desired negative pressure.

In Example 16, the subject matter of Example 10 optionally includes the desired pressure which can be a negative pressure, and wherein the control module can be configured to, in response to the decrease in the sensed pressure, control the irrigation source to provide an irrigation fluid to the suction channel at an irrigation flow rate such that the sensed pressure is maintained at substantially a level of the desired negative pressure.

Example 17 is an endoscopic surgical system that comprises: an endoscope including an imaging module, a surgical module, and at least one working channel configured to conduct an irrigation fluid or a suction pressure; a user input configured to receive from a user a desired pressure to be applied to an anatomical environment at an anatomical site in the patient; a flow sensor configured to sense a flow rate through the at least one working channel of the endoscope; a pressure sensor configured to sense a pressure of the anatomical environment at the anatomical site; and a control module configured to: detect a channel state using the sensed flow rate, the channel state indicating a presence or an absence of clogging in the at least one working channel; in response to, and for as long as, the detected channel state indicating a presence of clogging in the at least one working channel, control one or more of an irrigation source or a suction source to provide respectively an irrigation fluid or a suction pressure to unclog the at least one working channel; and adjust one or more of an irrigation flow rate or a suction flow rate through the at least one working channel to maintain the sensed pressure at substantially a level of the desired pressure.

Example 18 is a method of unclogging at least one working channel of a medical device during a procedure in a patient. The method comprises steps of: sensing a flow rate through the at least one working channel of the medical device via a flow sensor; detecting a channel state using the sensed flow rate via a control module, the channel state indicating a presence or an absence of clogging in the at least one working channel; and in response to the detected channel state indicating a presence of clogging in the at least one working channel, controlling one or more of an irrigation source or a suction source to provide respectively an irrigation fluid or a suction pressure to unclog the at least one working channel.

In Example 19, the subject matter of Example 18 optionally includes providing the irrigation fluid or the suction pressure to unclog the at least one working channel that can be continued for as long as the detected channel state indicating a presence of clogging in the at least one working channel.

In Example 20, the subject matter of any one or more of Examples 18-19 optionally includes detecting the channel state that can include steps of: detecting a presence of clogging in the at least one working channel in response to a decrease in the sensed flow rate below a first threshold; and detecting an absence of clogging in the at least one working channel in response to an increase in the sensed flow rate above a second threshold.

In Example 21, the subject matter of any one or more of Examples 18-20 optionally includes unclogging the at least one working channel that can include alternating between an application of irrigation fluid and an application of suction pressure to the at least one working channel.

In Example 22, the subject matter of any one or more of Examples 18-21 optionally includes steps of: receiving, via a user input, a desired pressure to be applied to an anatomical environment at an anatomical site in the patient; sensing a pressure of the anatomical environment at the anatomical site via a pressure sensor; and adjusting one or more of an irrigation flow rate or a suction flow rate through the at least one working channel such that the sensed pressure is maintained at substantially a level of the desired pressure.

In Example 23, the subject matter of Example 22 optionally includes steps of: receiving a desired flow condition in the at least one working channel, the desired flow condition corresponding to the desired pressure to be applied to the anatomical environment; and adjusting one or more of the irrigation flow rate or the suction flow rate through the at least one working channel to maintain the desired flow condition.

In Example 24, the subject matter of Example 22 optionally includes the at least one working channel that can include a suction channel and an irrigation channel. The method comprises steps of: in response to a presence of clogging in the suction channel, controlling the irrigation source to provide an irrigation fluid to the suction channel; in response to an increase in the sensed pressure of the anatomical environment at the anatomical site, controlling the suction source to apply a suction pressure to the irrigation channel to maintain the sensed pressure at substantially a level of the desired pressure; and in response to an absence of clogging in the suction channel, controlling the suction source to apply a suction pressure to the suction channel, and controlling the irrigation source to provide an irrigation fluid to the irrigation channel.

In Example 25, the subject matter of Example 22 optionally includes the at least one working channel that can include a suction channel and an irrigation channel. The method comprises steps of: in response to a presence of clogging in the irrigation channel, controlling the suction source to apply a suction pressure to the irrigation channel; in response to a decrease in the sensed pressure of the anatomical environment at the anatomical site, controlling the irrigation source to provide an irrigation fluid to the suction channel to maintain the sensed pressure at substantially a level of the desired pressure; and in response to an absence of clogging in the irrigation channel, controlling the suction source to apply a suction pressure to the suction channel, and controlling the irrigation source to provide an irrigation fluid to the irrigation channel.

This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 2A-2B are diagrams illustrating a powered tissue removal device 200 that may be used in the system as described in reference to FIG. 1.

FIG. 7B is a timing diagram of activating irrigation/suction in the irrigation channel during unclogging of an obstructed irrigation channel.

FIG. 7C is a timing diagram of activating irrigation/suction in the suction channel to maintain a desired pressure at the anatomical site during unclogging of an obstructed irrigation channel.

DETAILED DESCRIPTION

Figure 1:
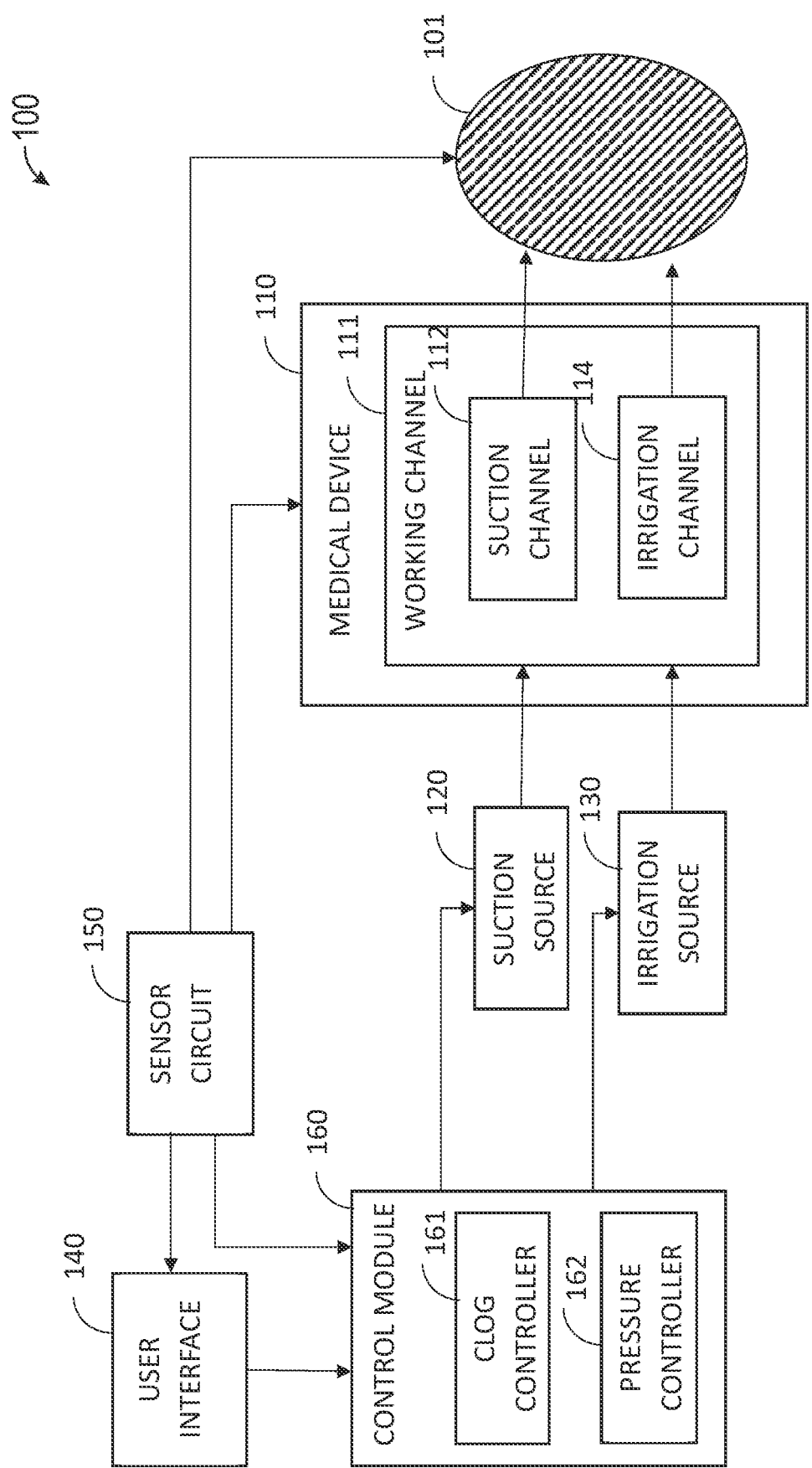
FIG. 1 is a block diagram illustrating an example of a system for in situ unclogging a working channel of an endoscope, and maintaining the pressure of an anatomical environment at the anatomical site at substantially a desired level during a minimally invasive procedure.

An endoscope comprises a tubular portion insertable into an interior of an organ or a cavity of the body to assist in diagnosis or treatment. One or more working channels (e.g., a suction channel and/or an irrigation channel) can be disposed inside, and extend along a length of, the tubular portion. To lower the risk of damaging unintended tissue, the insertable tubular portion may have a small diameter. Consequently, the working channels also have small lumen diameters. Because the tissue debris and foreign objects (e.g., calculi and fragments thereof) commonly have dimensions that are one to two lumen diameters in length, some tissue or stone particles can accumulate and clog the working channel.

In this document, "clog" refers to tissue debris, calculi (e.g., kidney stones or stone fragments) and other matter that accumulate and block the lumen of a channel partially or completely, and "clogging" refers to a state of partial or complete blockage of the channel lumen. Clogging may occur in any working channel of an endoscope. Clogging in a suction channel can significantly reduce the efficiency of removing the tissue debris and stone fragments therethrough. Delayed or inefficient removal of unwanted matters from the anatomical site can inhibit or prevent further treatment (e.g., debridement or ablation of stones), contaminate the anatomical site, and expose the patient at an increased risk. On the other hand, clogging in an irrigation channel may reduce the volume and/or the flow rate of irrigation fluid flowing therethrough and supplied to the anatomical environment. The slow irrigation flow can be less efficient in flushing out the unwanted matters from the anatomical site, and increase the likelihood of clogging in the suction channel. Reduced irrigation volume and flow rate may also affect its cooling effect on the surgical members and the anatomical environment, and increase the chance of heat accumulation at the anatomical site. Moreover, clogging in any working channel may block the lens of the endoscope, impair the visibility of the object under inspection, and reduce the quality of images taken at the anatomical environment, thereby increasing procedure difficulty and time.

Suction and irrigation can result in respectively negative and positive pressure changes on the anatomical environment at the anatomical site. Negative and positive pressure changes, if not properly controlled, may be harmful to internal organs exposed to the anatomical site. For example, while the body can regulate some positive pressure changes, many organs are relatively defenseless to negative pressure changes. Clogging in a working channel (e.g., a suction channel or an irrigation channel) may break the pressure balance between the positive pressure in association of the fluid flow and the negative pressure in association with the suction, thereby exposing the internal organ at the anatomical site to harmful excessive positive or negative pressures.

Various approaches have been attempted to prevent or resolve channel clogging in an endoscope. For example, breaking the unwanted matters (e.g., tissue debris or the stone fragments) into finer pieces can reduce the likelihood of being clogged in the channel. This, however, may consume more energy, take a longer procedure time, and potentially increase patient risk due to the added procedure complexity and time. The fine particles or stone dust may reduce visibility of the surgical field. Conventionally, unclogging is usually performed externally, which requires a clinician to retract the scope from the body, flush the obstructed scope to unclog it, and insert it back to the anatomical site. This approach increases procedure time, adds inconvenience to the clinician, and can increase surgical risks for the patient. In situ unclogging of a working channel when the endoscope remains inserted and hold in position generally require high-pressure irrigation, which may impose excessive positive pressure on the internal organ.

The present inventors have recognized an unmet need of endoscopic system capable of monitoring and stabilizing a desirable internal pressure automatically while enabling user input flow rates (e.g., a suction flow rate and/or an irrigation flow rate) to protect internal organs from pressure-related harms.

For at least the above reasons, the present inventors have recognized an unmet need for systems and methods that are capable of detecting a state of clogging in a working channel, unclogging the obstructed channel with increase efficiency, safety, and success of endoscopic procedures, while at the same time keeping the pressure change on the anatomical environment under control, for the duration of the procedure.

Disclosed herein systems and methods of in situ unclogging of a working channel in an endoscope, such as an irrigation channel or a suction channel, during an endoscopic procedure. According to one aspect of the present document, an unclogging system can detect a channel state indicating a presence or absence of clogging in the working channel using flow information sensed by a flow sensor, unclog the obstructed channel by applying irrigation fluid or suction pressure thereto, such as in an alternating fashion. The unclogging system can adjust one or more of an irrigation flow rate or a suction flow rate through one or more channels inside the endoscope to keep the pressure of the anatomical environment under control, such as to maintain a substantially net-zero pressure, or a desired positive pressure or a desired negative pressure as specified by the user, for the duration of the procedure.

The unclogging system and methods according to various embodiments discussed in this document provide an improved solution to in situ unclogging of an endoscope during an endoscopic procedure. In accordance with various aspects as described herein, the present systems and methods offer users endoscopy without repeated insertion and removal of endoscope attachment and accessories for external flushing and unclogging. Compared to unclogging via high-pressure irrigation which may put the internal organs at risk of high positive pressure, the controlled irrigation and suction applied to the same clogged channel as discussed in this document, such as in an alternating fashion, offers environmental stabilization of internal organs. Various embodiments of the present unclogging system can unclog the channel by effectively separating clog particles of different sizes that accumulate and block the channel, while avoiding or minimizing hazardous positive or negative pressure changes on the internal organs. As a result, unwanted matters can be safely and more efficiently removed from the anatomical site yet in a less invasive procedure, procedure time can be reduced, and patient safety and patient recovery time can be improved.

FIG. 1 is a block diagram illustrating an example of a system 100 for in situ unclogging a working channel of an endoscope during a minimally invasive procedure in a patient, while maintaining the pressure of an anatomical environment 101 at the anatomical site at substantially a desired level. The system 100 may include a medical device 110 and optional component(s). The optional component(s) can include any of a suction source 120, an irrigation source 130, a user interface 140, a sensor circuit 150, or a control module 160. In various examples, the system 100 can have a modular design that provides enhanced flexibility to allow easy configuration and replacement of an individual component. In an example, the user interface 140, the sensor circuit 150, and the control module 160 can be included in a suction/irrigation control unit. The suction/irrigation control unit can be fluidly coupled to one or more the device 110, the suction source 120, or the irrigation source 130. The suction/irrigation control unit can adapt to different types of medical device and different types of irrigation source and suction source. Exemplary suction/irrigation control units are discussed below with reference to FIGS. 3A-3B. The suction/irrigation control unit can selectively activate or deactivate irrigation and/or suction through the working channel 111, and adjust one or more of an irrigation flow rate, irrigation fluid pressure, a suction flow rate, or suction pressure. By controlling suction and/or irrigation in accordance with various embodiments discussed herein, the obstructed channel can be unclogged, and the pressure of the anatomical environment 101 can be maintained at a desired level during the procedure.

The medical device 110 can be used in diagnostic, analytical, or therapeutic applications, including, for example, minimally invasive surgeries such as endoscopic procedures. By way of example and not limitation, the medical device 110 may be used in joint surgery, plastic surgery, various otolaryngologic procedures, including but not limited to sinus surgery and tonsillectomy, or a combination thereof. The medical device 110 can be controlled by a user to perform a procedure in an organ in the anatomical environment 101 or to remove organ tissue. The controls of the medical device 110 may include a hand piece or indirect control, e.g., via a robotic surgery console or a user interface.

An example of the medical device 100 can include a tissue removal device comprising a blade assembly configured to rotate and/or reciprocate to excise unwanted tissue from target anatomy. The blade assembly may be driven by a motor powered by an energy source internal, or alternatively external, to the hand piece. The energy source may also fulfil other functions such as providing powered irrigation and suction to the medical device 110, as to be discussed below. Various blade assemblies can be used, including, for example, a shaver, a debrider, a blade, or a burr, among others. Depending on the blade assemblies used, the tissue removal device may function to shave, cut, abrade, or otherwise remove necrotic, cancerous, damaged, infected or otherwise unwanted soft tissue, bone, or other anatomical features or objects at or from the target anatomy. An exemplary tissue removal device is discussed below with reference to FIGS. 2A-2B.

Another example of the medical device 110 can include an endoscope. Examples of the endoscope can include a cystoscope for examining a urinary bladder, a nephroscope for examining a kidney, a bronchoscope for examining a bronchus, an arthroscope for examining joints, a colonoscope for examining a colon, a cholangioscope for examining biliary region (e.g., bile ducts), a duodenoscope for examining gastrointestinal region, or a laparoscope for examining abdomen or pelvis, among others. The endoscope may include a light source to illuminate the anatomical environment at the anatomical site, and an imaging module to produce images or video of the anatomical environment during the endoscopic procedure. Some endoscopes, such as an endoscopic tissue removal device, can include a tissue resection member configured to shave, cut, abrade, or otherwise remove portions of unwanted tissue from the target anatomy. The resected tissue debris can then be extracted from the anatomical site. Some endoscopes can include an ablation member configured to break or remove a foreign object, such as crystalline mineral structures, from the anatomical environment. For example, a nephroscope can be at least partially inserted into a kidney. Ultrasonic energy, electromagnetic shock waves, or lasers, among other energy modalities, may be delivered to kidney stones to break them into fragments or "stone dust", which can then be extracted from the anatomical site. An exemplary endoscope is discussed below with reference to FIGS. 3A-3B.

The medical device 110 can include one or more working channels 111 to transport the shaved, cut, resected, abraded, or removed tissue, bone, or the other anatomical features or objects, fragments of calculi and matter, body fluid at the anatomical site, and irrigation fluid, referred to herein collectively as "unwanted matters". The working channel 111 can be selectively coupled to one or more of the suction source 120 (such as via a suction port on the medical device 110) or the irrigation source 130 (such as via an irrigation port on the medical device 110).

The suction source 120 may function to pull, suck, draw, aspirate, or otherwise move or remove the unwanted matters from the anatomical site. The unwanted matters may be moved into a receptacle located at a proximal end of the medical device 110, inside the hand piece, or at a location away from the medical device 110. In an example, the hand piece may contain a container or reservoir for collecting, at least temporarily, the unwanted matters, before the hand piece being cleaned and the collected matter removed. The suction source 120 may perform the aforementioned functions by generating and applying vacuum, suction, or negative pressure to the working channel 111 of the medical device 110. In an example, the suction source 120 can be separate from the medical device 110, and connected thereto via one or more tubes, wires, or hoses. In another example, the suction source 120 can be included in or attached to the medical device 110. For example, the suction source 120 may be contained within the hand piece of a tissue removal device or an endoscope. The suction source may be powered by the energy source that also powers the medical device, or may be powered by its own energy source.

The irrigation source 130 may function to provide irrigation fluid to the working channel 111 to assist in the removal of unwanted matters (e.g., tissue debris or stone fragments) through the working channel 111. The irrigation fluid may also cool the tissue removal device or the resection elements during rotatory or reciprocated debridement or resection, and help dissipate the heat generated during stone fragmentation. The irrigation fluid may be gravity fed or pressurized. In an example, the irrigation source may comprise a bag that is elevated relative to the medical device 111 and the anatomical site to produce gravity-fed irrigation fluid. In another example, a pump may produce pressurized irrigation flow. The irrigation fluid can be provided from the irrigation source 130 or a location where the irrigation fluid is contained, to and through an external fluid supply tube, and drawn into the working channel 111. Under a suction pressure provided by the suction source 120, the irrigation fluid, along with the unwanted matters, can flow towards a proximal direction of the working channel 111 and removed from the anatomical site.

In an example, a single working channel 111 can be used for both irrigation and suction. The control module 160 can controllably activate irrigation and suction through the working channel 111 at separate times. In another example, the medical device 110 may include two or more separate working channels, such as a suction channel 112 and an irrigation channel 114, as illustrated in FIG. 1. The suction channel 112 can be controllably connected to the suction source 120 to conduct the unwanted matters being sucked therethrough. The irrigation channel 114 can be controllably connected to the irrigation source 130 to conduct irrigation fluid therethrough. In an example, the suction channel 112 can be controllably connected to the irrigation source 130. In an example, the irrigation channel 114 can be controllably connected to the suction source 120. Irrigation and suction according to various examples discussed herein can be used to assist in removing unwanted matters, unclogging one or more working channels, transferring the heat generated during the procedure at the tissue site, maintaining the pressure of the anatomical environment at a desired level, and maintaining a desired flow condition in the working channel that corresponds to the desired pressure, among others.

In an example, the suction channel 112 and the irrigation channel 114 can be disposed in a parallel orientation along a length of a tubular portion of the hand piece of the medical device 110. In an example, the suction channel 112 and the irrigation channel 114 can be coaxially disposed with a common axis, such as in a nested configuration. In an example, the medical device 110 comprises an outer member, and an inner member located within the outer member. The suction channel 112 can be located inside the inner member. The irrigation channel 114 can be located outside of the outer member. In some configurations, in addition to or in lieu of supplying irrigation fluid through the irrigation channel 114, the irrigation fluid may be supplied through a gap defined between the inner and outer members of the medical device 110, hereinafter referred to as an "irrigation gap". One of the irrigation channel 114 or the irrigation gap may be selectively activated to supply irrigation fluid to the medical device 110. In some examples, both the irrigation channel 114 and the irrigation gap can be activated to supply irrigation fluid simultaneously. This may advantageously allow a clinician to regulate how much irrigation fluid is used during a procedure. For example, when more tissue debris or stone fragments are produced, or if clogging is detected in a channel, both the irrigation channel 114 and the irrigation gap can be activated to provide a larger volume of fluid to the medical device 110.

The control module 160 can be configured to control the operation of the medical device 110, including one or more of tissue resection or stone ablation, illumination, imaging, irrigation, and suction, among other functionalities during an endoscopic procedure. In an example, the control module 160 may be implemented as a part of a microprocessor circuit, such as a dedicated processor, application specific integrated circuit (ASIC), microprocessor, or other type of processor for processing information, generating control signals to activate, deactivate, or change the operation of a component of the system 100. Alternatively, the microprocessor circuit may be a processor that may receive and execute instructions of performing the functions, methods, or techniques described herein.

Figure 3A:
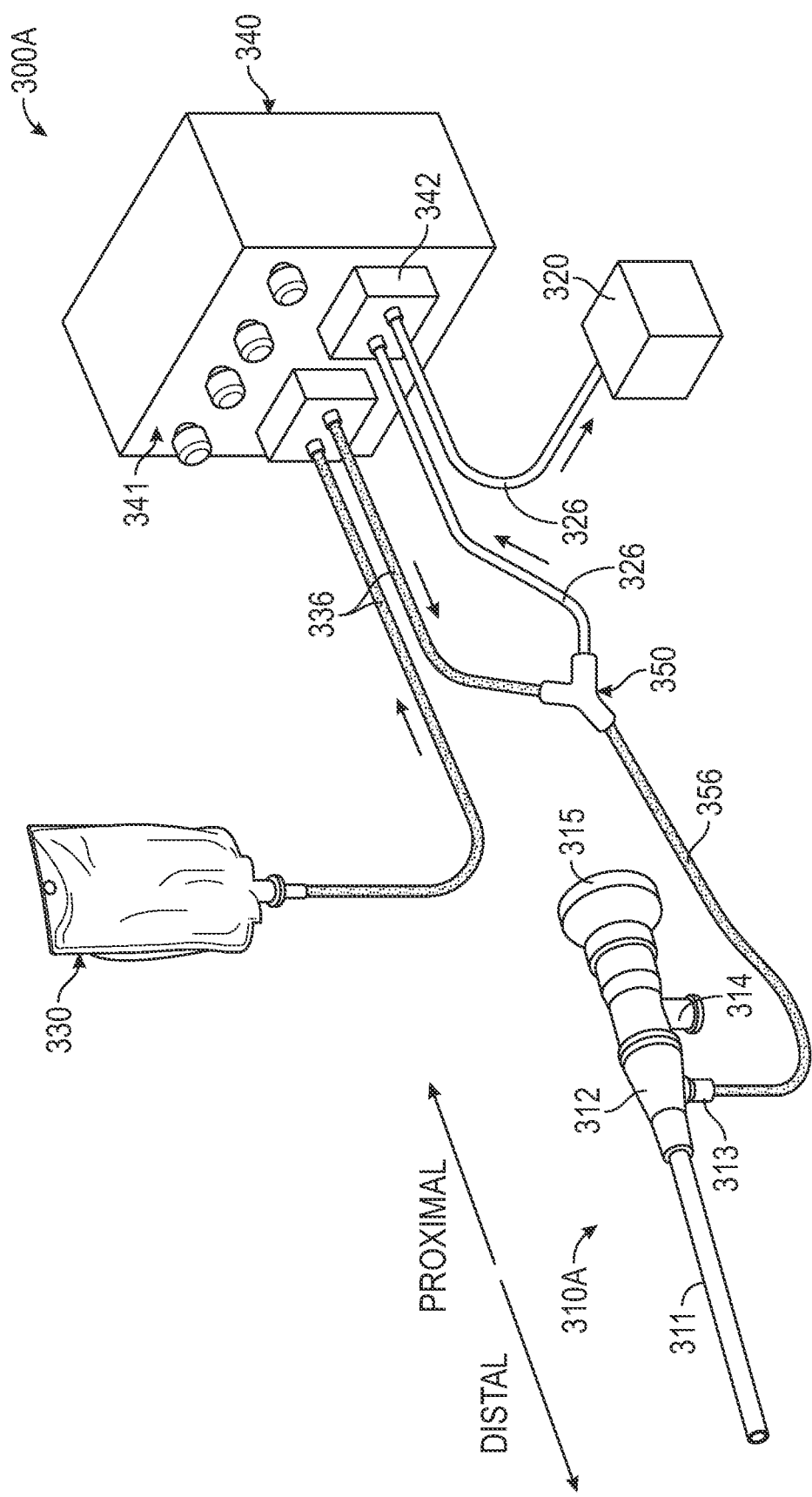
FIGS. 3A-3B are diagrams illustrating endoscope systems for unclogging an obstructed channel and maintaining the pressure of an anatomical environment at substantially a desired level during an endoscopic procedure.
Figure 3B:
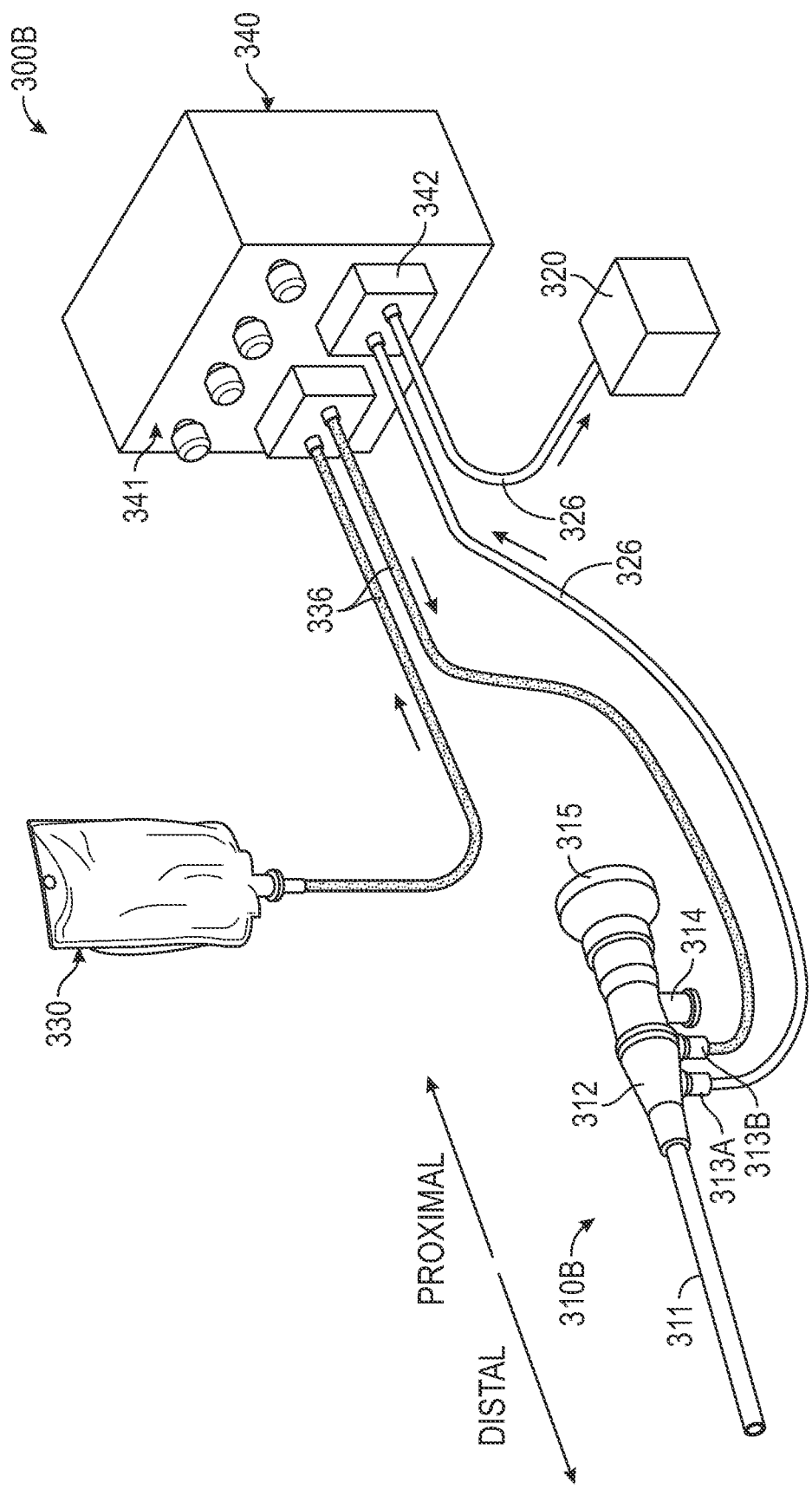

The control module 160 may be at least partially implemented in a unit separate from the medical device 110, such as that illustrated in FIGS. 3A-3B. Alternatively, portions of the control module 160 may be integrated into or otherwise attached to the medical device 110. In some examples, the control module 160 may include circuit sets that, alone or in combination, perform the functions, methods, or techniques described herein. In an example, hardware of the circuit set may include invariably connected components designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

As illustrated in FIG. 1, the control module 160 can be coupled to a user interface 140, and receive therefrom user commands for activating, deactivating, or adjusting one of more functionalities of the medical device 110. The user interface 140 may be at least partially integrated into or otherwise attached to the medical device 110. Alternatively, the user interface 140 may be separate from the medical device 110, as an exemplary system illustrated in FIGS. 3A-3B. The user interface 140 can be mobile, and can be attached to the medical device 110 and fluid system (e.g., pump, irrigation). In an example, the user interface 140 may include one or more user controls that allow a user (e.g., a clinician) to turn ON or OFF suction, or to adjust suction flow rate or suction pressure. The user controls may be located on the mobile user interface separate from the medical device 110. Alternatively, the user controls may be located on the medical device 110, such as a hand piece of an endoscope or a tissue removal device, such as the device illustrated in FIG. 2A. The control module 160, in response to the user command, can activate or deactivate suction flow from the suction source 120, or to increase or decrease the suction pressure applied to the working channel 111 to achieve the desired suction flow rate. Similarly, the user interface 140 may include one or more user controls that allow the user to turn ON or OFF irrigation, or to adjust irrigation flow rate or irrigation fluid pressure (e.g., via a pump). The control module 160, in response to the user command, can activate or deactivate irrigation flow from the irrigation source 130, or to increase or decrease the irrigation flow rate through working channel 111.

In some examples, the user controls on the user interface 140 can include a depressible flushing control button that, when depressed repeatedly, cycles through one or more irrigation levels and/or suction levels, before turning off the irrigation and suction. In some examples, irrigation and suction can be controlled together with a single control. Other suitable control elements can also be used, such as a positionable slide, a positionable lever, or a positionable dial that can specify an irrigation level and/or a suction level. In some examples, the user interface 140 may allow a user to select from one of a plurality of specified discrete irrigation levels or suction levels, or alternatively specify the irrigation level or the suction level in a continuous (e.g., a non-discrete) manner.

In addition to or in lieu of independent control of suction and irrigation, the control module 160 may automatically control one of the irrigation or suction based on a status of the other of the irrigation or suction. In an example, the control module 160 may turn ON suction automatically when the medical device is powered, or when the irrigation source 130 supplies irrigation fluid to the medical device 110; and turn OFF suction automatically when the medical device is not powered, or when the irrigation source 130 ceases to supply irrigation fluid to the medical device 110. In an example, the control module 160 may automatically adjust the irrigation flow rate or fluid volume (e.g., by activating or deactivating flow in the irrigation gap defined between the inner and outer members) in response to the suction flow rate. For example, at an increased suction (e.g., due to a large amount of unwanted matters to be removed), the control module 160 may automatically increase the irrigation flow rate, or supply irrigation fluid via both the irrigation channel 114 and the irrigation gap. Conversely, at a reduced suction (e.g., due to a small amount of unwanted matters to be removed), the control module 160 may automatically decrease the irrigation flow rate, or supply irrigation fluid via only one, but not both, of the irrigation channel 114 or the irrigation gap.

The control module 160 can include a clog controller 161 configured to detect a channel state indicating a presence or an absence of clogging in the working channel 111, and control one or more of the suction source 120 or the irrigation source 130 to provide respectively suction pressure or irrigation fluid to unclog the obstructed working channel. In an example, the clog controller 161 can monitor the channel state and detect channel clogging based on flow information in the working channel 111. The sensor circuit 150 may include circuitry coupled to a flow sensor positioned inside the working channel 111 and configured to sense a flow rate or volume of a moving liquid therein. The flow sensor, such as a Micro Electro-Mechanical System (MEMS) sensor, can employ various flow-measuring techniques. By way of example and not limitation, the flow sensors may include thermal anemometers that measure a transfer rate of heat generated from a heat source, differential pressure sensors that measure pressure drop over a range of locations, ultrasonic flow sensors that measures the Doppler effect of frequency shift or time-of-travel/flight, electromagnetic sensors that measure a change in fluid conductance indicative of flow rate, among others.

The clog controller 161 can detect channel clogging using the flow rate information sensed by the flow sensor. In an example, the clog controller 161 can detect channel clogging in response to a decrease in the sensed flow rate, such as below a first flow rate threshold; and can detect an absence of clogging, or a successful unclogging of an obstructed working channel, if the sensed flow rate increases and exceeds a second flow rate threshold. In another example, channel clogging can be detected using stability of flow rate inside the channel, such as when a variability of flow rate measurements exceeds a threshold. In some examples, the clog controller 161 can detect channel clogging by comparing an inflow rate of the fluid entering the channel and an outflow rate of the fluid leaving the channel. A mismatch between the inflow and outflow rate, such as an outflow rate being substantially lower than the inflow rate (exceeding a specified tolerance), indicates the presence of channel clogging.

Figure 4A:
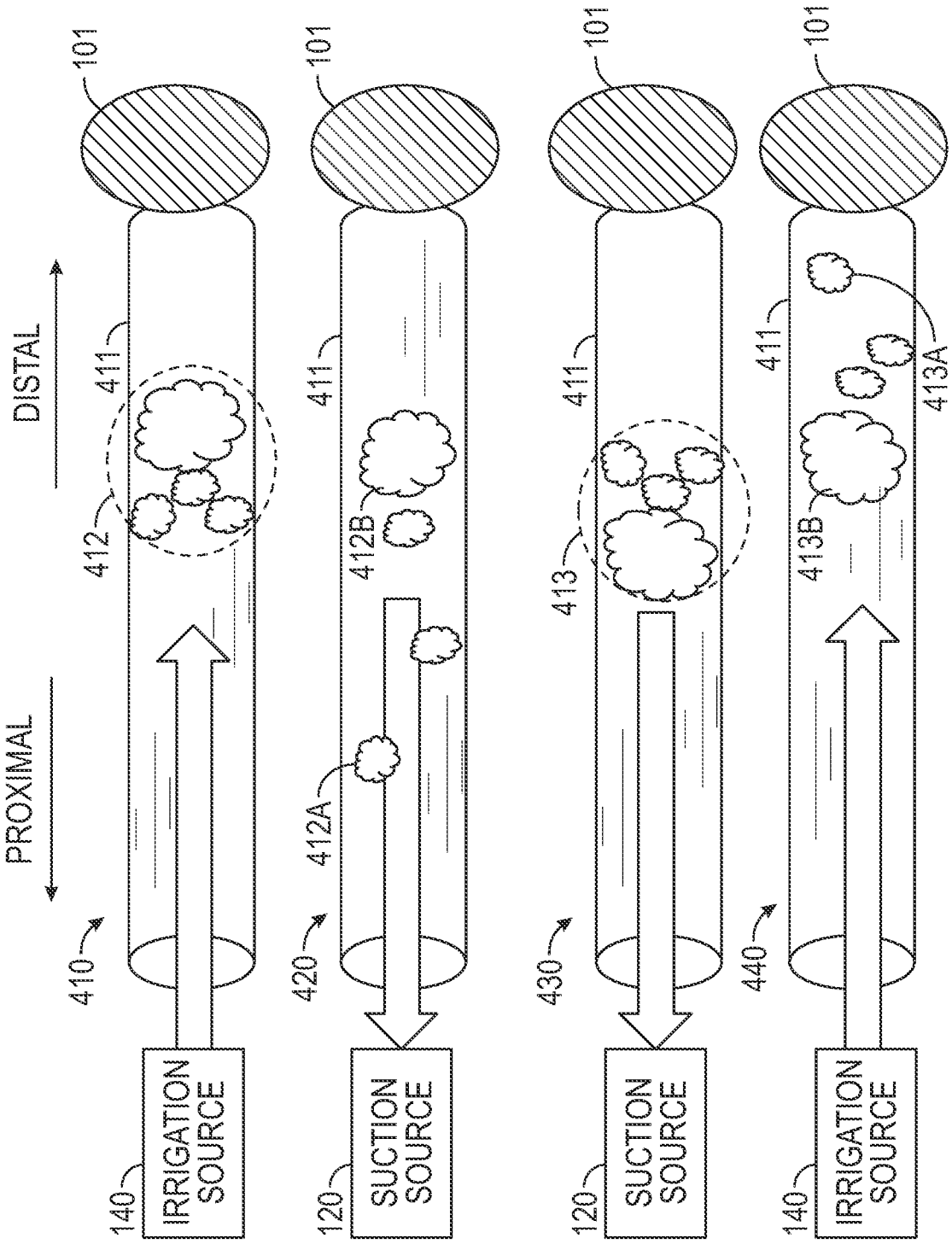
FIG. 4A illustrates exemplary techniques for unclogging an obstructed working channel of an endoscope in accordance with an embodiment discussed in this document.

In the presence of channel clogging, the clog controller 161 can automatically switch from a standard mode of irrigation/suction operation as discussed above (e.g., where the suction source 120 provides suction pressure to the suction channel 112, and the irrigation source 130 provides a flow of irrigation fluid to the irrigation channel 114), to an unclogging mode of irrigation/suction operation. To unclog an obstructed channel, the clog controller 161 can alternate between an application of irrigation fluid and an application of suction pressure to the obstructed channel. Referring now to FIG. 4A, the diagrams therein illustrate a channel unclogging technique in accordance with an embodiment discussed in this document. Diagram 410 illustrates a fluid-filled channel 411 obstructed by a clog 412 during a standard mode of irrigation activated by the irrigation source 140. The clog 412 comprises tissue debris or stone fragments of different sizes. As illustrated in diagram 410, smaller particles such as particle 412A are proximally located, and larger particles such as particle 412B are distally located. Diagram 420 illustrates switching from the standard mode to an unclogging mode, in which clog controller 161 fluidly couples the suction source 120 to the proximal portion of the channel 411, activates the suction source 120, and applies suction pressure thereto for a specified suction duration. The user can adjust the suction pressure and the suction duration via the user interface 140. The clog particles of different sizes (thus different masses) may respond differently to the suction pressure applied. For example, the smaller particle 412A may move towards the proximal end of the channel at a faster speed and travel for a longer distance during (and after) the application of suction than the larger particle 412B. As a result, some particles may be dislodged from the clog 412 and separated from the larger particles.

Diagram 430 illustrates the fluid-filled channel 411 obstructed by a clog 413 during a standard mode of suction activated by the suction source 120. Particles of the clog 413 accumulate differently from the clog 412, where smaller particles such as particle 413A are distally located, and larger particles such as particle 413B are proximally located. Diagram 440 illustrates switching from the standard mode to an unclogging mode, in which the clog controller 161 fluidly couples the irrigation source 140 to the proximal portion of the channel 411, activates the irrigation source 140, and applies irrigation fluid to flush the channel 411 for a specified irrigation duration. The user can adjust the irrigation flow rate, or a pressure to pump the irrigation fluid, and the irrigation duration. The clog particles of different sizes (thus different masses) may respond differently to the flushing irrigation fluid. For example, the smaller particle 413A may move towards the distal end of the channel at a faster speed and travel for a longer distance during (and after) the application of irrigation than the larger particle 413B. As a result, some particles may be dislodged from the clog 413 and separated from the larger particles.

The separated particles may be extracted down the working channel 411 using additional irrigation and/or suction. In an example, one or more of the suction pressure, the suction flow rate, the irrigation flow rate, or the pump pressure for pressurizing the irrigation fluid, can be varied (such as via the user interface 140) to separate out particles by size. For example, a higher flow rate can be applied to remove larger particles, and a lower flow rate can be applied to remove smaller particles through the channel 411.

Figure 4B:
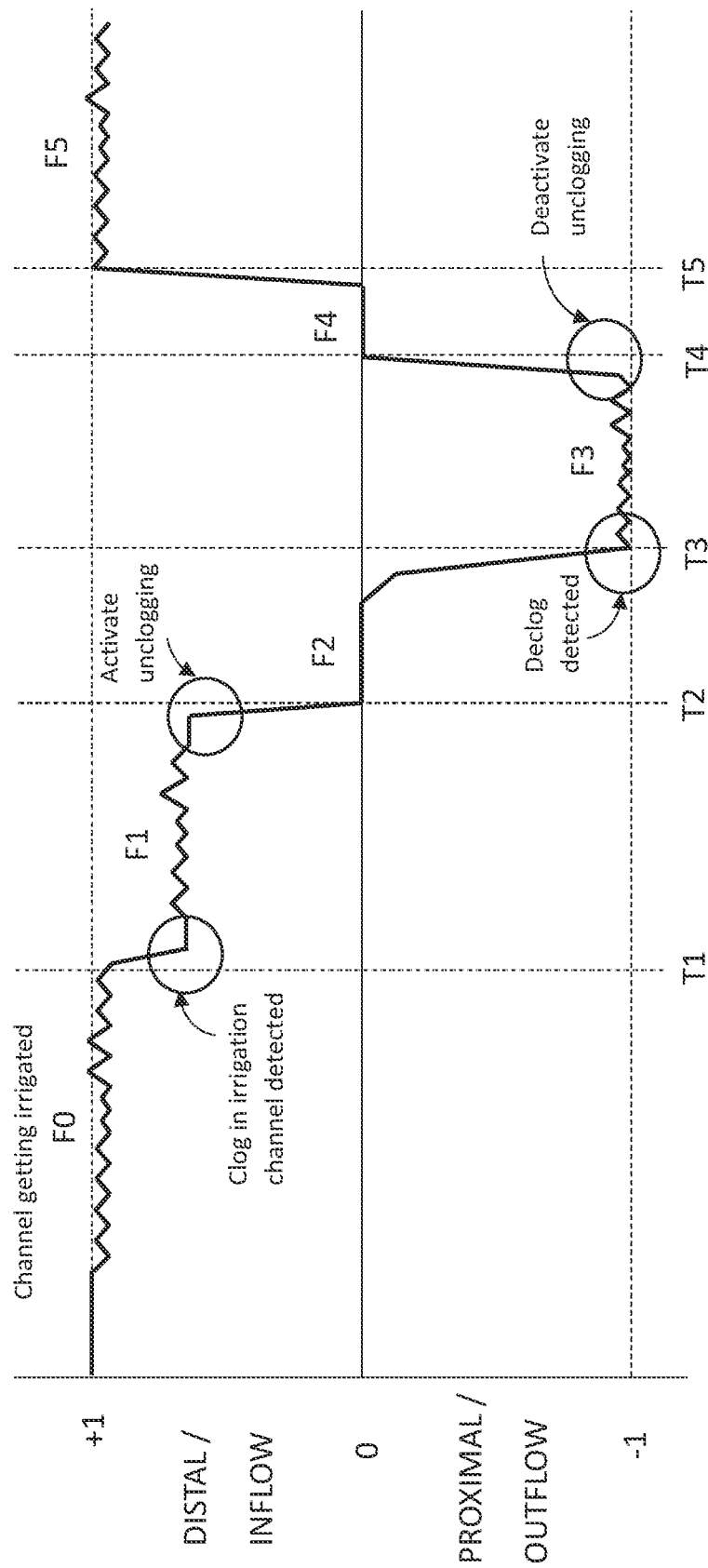
FIG. 4B-4C are diagrams illustrating a change in flow in a working channel in the presence of clogging and during the unclogging process.
Figure 4C:
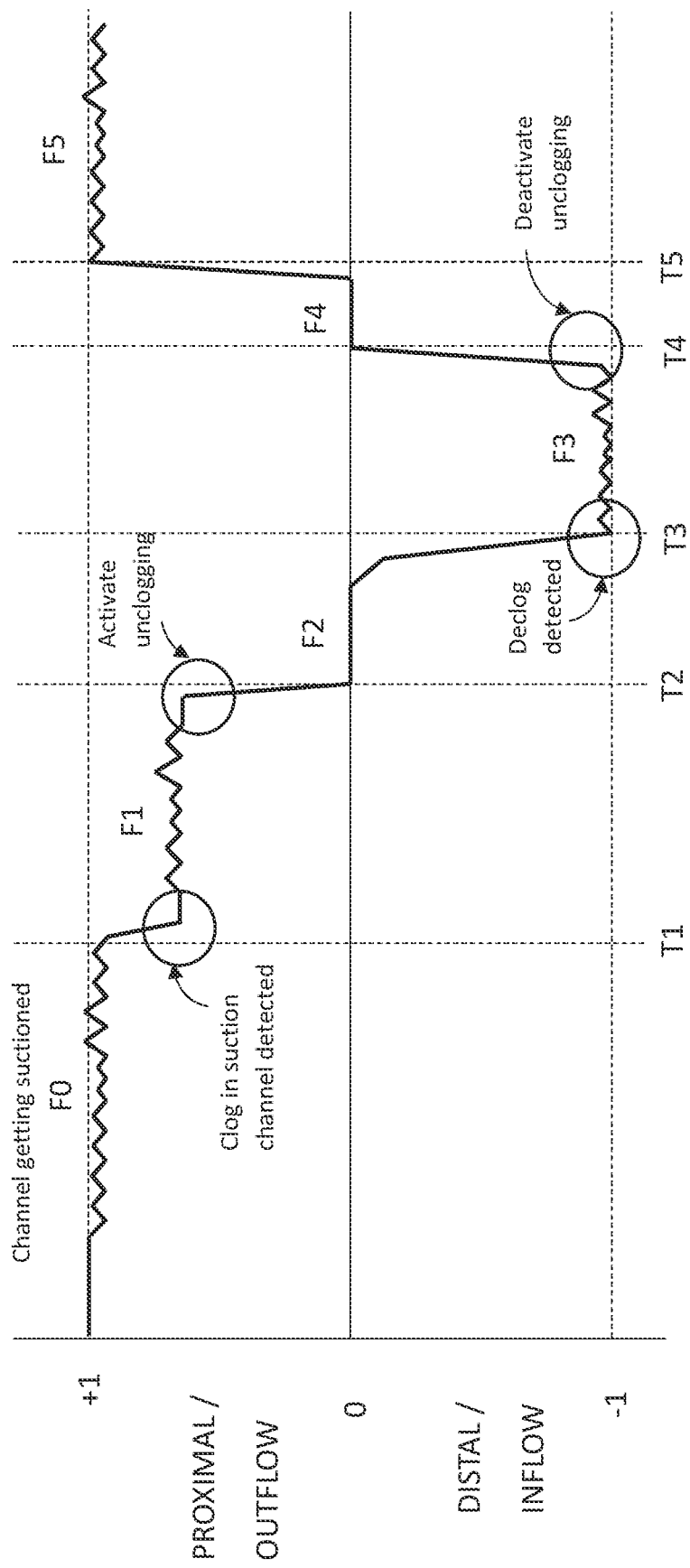

FIGS. 4B-4C are diagrams illustrating a change in flow in a working channel in the presence of clogging and during the unclogging process. FIG. 4B illustrates flow change in a clogged irrigation channel, as illustrated in diagrams 410 and 420 of FIG. 4A. Flow parameters, such as a flow rate, can be measured using a flow sensor disposed in the irrigation channel. The flow measurement (in the y-axis) has a value between −1 and 1. A positive flow value represents a flow direction towards the distal end of the suction channel (or towards the anatomical environment 101, see diagram 410 of FIG. 4A). A negative flow value represents the opposite direction, that is, a flow towards the proximal end of the suction channel (or away from the anatomical environment 101, see diagram 420 of FIG. 4A). Values of the flow measurement is relative to an unobstructed flow through the irrigation channel. That is, a flow value of "1" represents a flow during irrigation of an unobstructed channel, and a flow value of "−1" represents a flow during suction of the unobstructed channel.

During a standard mode of irrigation of an unclogged irrigation channel, a positive flow F0 of a value of approximately "1" can be detected by the flow sensor. As illustrated, the flow F0 includes fluctuations superposed on constant flow, indicating small fragments being suctioned. At T1, the flow rate decreases to F1 (less than F0). A clogging is detected if the decrease F0-F1 exceeds a clog detection threshold. In this example, F1 is at a level greater than zero, indicating the channel is not completely blocked, and the irrigation is continued. The particles continue to build up, until the flow rate drops to F2 at T2. F2 is approximately zero, indicating a substantial channel blockage (as illustrated in diagram 410 of FIG. 4A). An unclogging mode can be activated at T2, or at a time corresponding to a particular (e.g., user-specified) flow condition. Suction can be applied to the obstructed channel, drawing fluid and mass therein towards the proximal end of the suction channel (as illustrated in diagram 420 of FIG. 4A). A negative flow F3 can be sensed by the flow sensor. As discussed above with reference to diagram 420 of FIG. 4A, the suction can break down the clog, such that particles of smaller sizes can be dissociated with the rest of the clog and travels towards the proximal end of the channel for a longer distance. Suction can be continued as the channel is being unclogged, allowing the negative flow F3 to reach approximately the maximum ("−1", indicating substantially unobstructed flow) at T3. After application of suction for a specified period of suction time and the dislodged particles are extracted out of the channel, suction can be stopped at T4. The negative flow rate can then decrease to a substantially zero flow F4. At T5, standard irrigation mode resumes by applying irrigation fluid to the unclogged channel. As the channel is successfully unclogged and particles removed from the channel, a positive flow F5 of a value of approximately "1" can be sensed by the flow sensor.

FIG. 4C illustrates flow change in a clogged suction channel, as illustrated in diagrams 430 and 440 of FIG. 4A. Flow parameters, such as a flow rate, can be measured using a flow sensor disposed in a suction channel. The flow measurement (in the y-axis) has a value between −1 and 1. A positive flow value represents a flow direction towards the proximal end of the suction channel (or away from the anatomical environment 101, see diagram 430 of FIG. 4A). A negative flow value represents the opposite direction, that is, a flow towards the distal end of the suction channel (or towards the anatomical environment 101, see diagram 440 of FIG. 4A). Values of the flow measurement is relative to an unobstructed flow through the suction channel. That is, a flow value of "1" represents a flow during suction of an unobstructed channel, and a flow value of "−1" represents a flow during irrigation of the unobstructed channel.

During a standard mode of suction applied to an unclogged suction channel, a positive flow F0 of a value of approximately "1" can be detected by the flow sensor. As illustrated, the flow F0 includes fluctuations superposed on constant flow, indicating small fragments being suctioned. At T1, the flow rate decreases to F1 (less than F0). A clogging is detected if the decrease F0-F1 exceeds a clog detection threshold. In this example, F1 is at a level greater than zero, indicating the channel is not completely blocked, and the suction is continued. The particles continue to build up, until the flow rate drops to F2 at T2. F2 is approximately zero, indicating a substantial channel blockage (as illustrated in diagram 430 of FIG. 4A). An unclogging mode can be activated at T2, or at a time corresponding to a particular (e.g., user-specified) flow condition. Irrigation fluid can be injected into the obstructed channel towards the distal end of the suction channel and towards the anatomical environment (as illustrated in diagram 440 of FIG. 4A). A negative flow F3 can be sensed by the flow sensor. As discussed above with reference to diagram 440 of FIG. 4A, the irrigation fluid can break down the clog, such that particles of smaller sizes can be dissociated with the rest of the clog and travels towards the distal end of the channel for a longer distance. Irrigation is continued as the channel is being unclogged, allowing the negative flow F3 to reach approximately the maximum ("−1", indicating substantially unobstructed flow) at T3. After application of irrigation for a specified period of irrigation time, irrigation can be stopped at T4. The negative flow rate can then decrease to a substantially zero flow F4, as the separated particles settle down in the channel. At T5, standard suction mode resumes by applying additional suction to extract the dislodged particles out of the channel. As the channel is successfully unclogged and particles removed from the channel, a positive flow F5 of a value of approximately "1" can be sensed by the flow sensor.

In some examples, suction pressure and irrigation fluid may be applied to the channel 411 repeatedly in an alternating fashion. This allows more efficient separation of particles of the clog without a prior knowledge of, or a need to determine, the structure of the clog 412. Also, continuously applying suction and then occasional irrigation may help reduce the incidences of clog formation. The sensor circuit 150 may monitor the flow rate while the alternating suction and irrigation are applied repeatedly. The unclogging operation, including application of the irrigation fluid or the suction pressure to the obstructed channel, can be continued for as long as the channel clogging remains present. When the monitored flow rate increases and exceeds a threshold, the obstructed channel is deemed unclogged successfully.

The clog controller 161 can switch from the unclogging mode of operation back to the standard mode of irrigation/suction operation.

Referring back to FIG. 1, the control module 160 can include a pressure controller 162 configured to keep the pressure of the anatomical environment (also referred to as the "environmental pressure") under control, such as to maintain the environmental pressure at substantially a desired pressure level (e.g., a predetermined level, or as specified by a user via the user interface 140). In an example, the environmental pressure is deemed to be maintained at the desired pressure level if the difference between the environmental pressure measurement (such as by a pressure sensor) and the desired pressure falls within a range of tolerance, e.g., ±5-10% as a non-limiting example. A desired pressure level to be maintained at the anatomical site of the anatomical environment 101 can be received from the user interface 140. As stated previously, suction may result in a negative pressure change at the anatomical site, while irrigation may result in a positive pressure change at the anatomical site. Negative and positive pressure changes may pose adverse effect on internal organs exposed to the anatomical site. Maintaining the environmental pressure at a controlled pressure level can increase patient safety and effectively reduce procedure time. In some examples, in addition to or in lieu of receiving a desired pressure level, a desired flow condition can be received, such as from the user interface 140. The desired flow condition includes information about inflow (e.g., a flow rate of irrigation fluid applied to the anatomical environment) relative to outflow (e.g., a flow rate of suction applied to the anatomical environment). The desired flow condition corresponds to the desired pressure to be applied to the anatomical environment. For example, a desired flow condition of substantially equal inflow rate and outflow rate corresponds to a substantially net-zero environmental pressure, a desired flow condition of a higher inflow rate than outflow rate corresponds to a positive environmental pressure, and a desired flow condition of a lower inflow rate than outflow rate corresponds to a negative environmental pressure. The pressure controller 162 can control one or more of an irrigation flow rate or a suction flow rate through one or more working channels to maintain the desired flow condition during the procedure.

The pressure controller 162 can achieve the controlled pressure by automatically activating, deactivating, or adjusting one or more of suction or irrigation. The sensor circuit 150 can monitor the pressure of the anatomical environment (the "environmental pressure") during the endoscopic procedure. In an example, the sensor circuit 150 can be coupled to a pressure sensor to sense the environmental pressure, or a signal indicative of or otherwise correlated to the environmental pressure. Examples of the pressure sensor can include resistive, capacitive, piezoelectric, optical, or Micro Electro-Mechanical System (MEMS) pressure sensors. In an example, the pressure sensor may be attached to or integrated into a distal portion of the medical device 110, such as a distal tip of an insertable tubular portion of an endoscope, such that the pressure sensor is in contact with the anatomical environment 101. In an example, the pressure sensor may be positioned at a more proximal location inside the tubular portion of the endoscope away from the anatomical environment 101. The control module 160 can receive from the user interface 140 a desired environmental pressure to be maintained during the procedure. The control module 160 can compare the sensed environmental pressure to the desired environmental pressure, and adjust one or more of an irrigation flow rate or a suction flow rate to drive the environmental pressure towards a level of the desired environmental pressure.

The pressure controller 162 can maintain the controlled environmental pressure when the system 100 operates in the standard mode of irrigation/suction (when no clogging is detected in any working channel) and in the unclogging mode of irrigation/suction (when at least one, but not all, of the working channels are clogged). Exemplary systems for regulating the environmental pressure via automatic adjustment of suction and/or irrigation flow rates are discussed below with reference to FIG. 5 (in the absence of channel clogging) and FIGS. 6-7 (in the presence of channel clogging).

The user interface 140 may include an output unit, such as a display, to present information collected during the endoscopic procedures including, for example, images (including live video) of the surgical field, operating status of the medical device 110 including status of the working channel 111, information about channel state such as a clogged channel or successful unclogging, and environmental pressure as sensed by the sensor circuit 150, among others.

FIG. 2A illustrates a perspective view of a powered tissue removal device 200, which is an example of the medical device 110. The powered tissue removal device 200 can include a hand piece 210 and a tubular assembly 222 extending from the hand piece 210. The tubular assembly 222 comprises a proximal portion 226 located at the hand piece 210, and an opposing distal portion 228. While the distal portion 228 is illustrated as being a "straight shaft" aligned with the rest of the tubular assembly 222, in some examples, the distal portion 228 may be bent or angled relative to the rest of the tubular assembly 222, including the proximal portion 226.

An exemplary configuration of the distal portion 228 is illustrated in FIG. 2B. The tubular assembly 222 comprises an outer tubular member 252 and an inner tubular member 254 that is located inside of the outer tubular member 252. The outer member 252 comprises an outer member window 262. The inner member 254 comprises a cutting portion 264 and a suction channel 274 defined inside the inner member 254. The inner member 254 or the cutting portion 264 comprises an inner member window 266 that is in communication with the suction channel 274.

The powered tissue removal device 200 comprises an irrigation channel 272 located external to, or outside of, the outer member 252. The irrigation channel 272 extends along a length of the outer member 252. A proximal end of the irrigation channel 272 comprises a proximal irrigation port 282 that is in fluid communication with the irrigation source 230, and a distal end of the irrigation channel 272 comprises a distal irrigation port 284 that is attached to the powered tissue removal device 200 or the outer member 252.

The powered tissue removal device 200 can be coupled to an energy source 240, a suction source 220, and an irrigation source 230. The energy source 240 is configured to power the powered tissue removal device 200, the suction source 220, the irrigation source 230, or a combination thereof. The suction source 220, which is an embodiment of the suction source 120, can be in fluid communication with the suction channel 274 defined inside the inner member 254. The suction source 220 is configured to apply suction to, or pull vacuum from, the powered tissue removal device 200 via the suction channel 274. The irrigation source 230, which is an embodiment of the irrigation source 130, can be in fluid communication with the irrigation channel 272 located external to or outside of the outer member 252. The irrigation source 230 can alternatively or additionally be in fluid communication with a gap between the inner member 254 and the outer member 252.

The powered tissue removal device 200 includes one or more user controls 224 for operating the powered tissue removal device 200, the energy source 214, the suction source 220, the irrigation source 230, or a combination thereof. By way of example and not limitation, the user controls 224, which are embodiments of the user interface 140, can be located at the hand piece 210 to allow easy access and manipulation by the user during a procedure. In an example, the user controls 224 may allow a user to manually control the debridement, activate, deactivate, or adjust one or more of an irrigation flow rate or a suction flow, among other irrigation or suction parameters.

The powered tissue removal device 200 includes a control module (not shown) at least partially located inside the hand piece 210. The control module, which can be an embodiment of the control module 160, can be configured to control the operation of the powered tissue removal device 200 in response to user commands from the user controls 240, including one or more of tissue debridement, irrigation, suction, among other functionalities. In an example, the control module can detect clogging in a working channel (e.g., a unified irrigation/suction channel, or a separate irrigation channel or a separate suction channel) based on a flow rate sensed from the working channel, and unclog the obstructed channel such as by alternating between an application of irrigation fluid and an application of suction pressure to the obstructed channel. The control module may active and adjust one or more of irrigation flow parameters or one or more suction flow parameters to keep the pressure of the anatomical environment (the "environmental pressure") under control, such as to maintain the environmental pressure at substantially a user-specified desired pressure during the procedure, as discussed above with reference to FIG. 1.

FIGS. 3A-3B illustrate respectively, by way of example, endoscope systems 300A and 300B, for use in an endoscopic procedure. The endoscope systems 300A and 300B are embodiments of the system 100. Referring to FIG. 3A, the system 300A comprises an endoscope 310A, a suction source 320, an irrigation source 330, and a suction/irrigation control unit 340. The endoscope 310A, which is an example of the medical device 110, can extend into a sheath including a tube 311 extending from a distal end to a hub 312. The hub 312 terminates at a proximal end. The endoscope 310A can include a light port 314 and a visual port 315. The light port 314 may function to provide light into the endoscope, and out of the tube 311 of the endoscope, such that a feature of interest in the anatomical environment (e.g., resected tissue or calculi and matter) is illuminated. The light port is advantageous to enhance visibility, for instance, when the feature of interest is located in low light conditions. The visual port 315 may function to provide a viewing window that allow a user to observe a feature of interest. In an example, the visual port 315 may be an optical window at the proximal end that provides visual access to a viewing lens at the distal end. In another example, the visual portion 315 may provide a connection point to a camera to take images or video of the feature of interest and the anatomical environment. The images or video can be output and displayed on a monitor.

The endoscope 310A can include an irrigation/suction port 313 for receiving suction or irrigation fluid. The irrigation/suction port 313 can be located on an exterior of the hub 312, or other locations on the endoscope 310A such as a proximal end of the endoscope 310A. The irrigation/suction port 313 is open to a working channel (not shown) inside the tube 311. The working channel can be sized, shaped, and configured to transport irrigation fluid and/or for suction. In an example, the same working channel can be used for irrigation and suction (also referred to as a unified irrigation/suction channel). In another example, an irrigation channel and a suction channel are separately disposed within the tube 311.

In an example, the endoscope 310A can be a nephroscope. During use, a flexible distal portion of the tube 311 may be surgically inserted into the kidney of the patient. The proximal portion of the tube 311 can remain outside the body of the patient. Inside the tube 311 can include an optical fiber extending along the length of the endoscope 310A. The optical fiber can be a multi-mode fiber or a single-mode fiber. A laser, external to the nephroscope, can generate the laser beam. The laser beam can be coupled into a proximal end of the optical fiber via a suitable connector. The optical fiber can deliver laser beam to the kidney stone to ablate the kidney stone into fragments. In some examples, the laser beam can have a wavelength that corresponds to a spectral peak of absorption of human blood and saline, such as 2100 nm, 1942 nm, and others. In general, delivering laser beam that has significant absorption in blood and saline can be beneficial, because such laser beam can be minimally invasive on surrounding tissue, which can reduce or eliminate damage to the tissue at or near the kidney stone. A laser controller can be located on a graspable proximal portion of the endoscope 310A. Similar to the user controls 224 that enables a manual control of the debridement as illustrated in FIG. 2A, the laser controller can allow a user to toggle a state of the laser beam between an operational state ("ON") and a non-operational state ("OFF"). In some examples, a user can adjust one or more settings of the laser, such as the output power, on a housing of the laser, rather than via the laser controller.

The suction/irrigation control unit 340 can provide suction and irrigation to the endoscope 310A during an endoscopic procedure, while keeping the pressure of the anatomical environment under control, such as to maintain the pressure at substantially at a user-specified pressure level (e.g., the user-specified pressure with a tolerance such as ±5-10%). The suction/irrigation control unit 340 can include a pressure monitor (which is an embodiment of the sensor circuit 150), a control module (which is an embodiment of the control module 160), a pump, a power source. The control module can be in communication with a user interface 341 (which is an embodiment of the user interface 140), such as located on an exterior of the suction/irrigation control unit 340, for controlling the control module.

The suction source 320 can be connected to suction/irrigation control unit 340 via an external suction line 326. The suction/irrigation control unit 340 includes a control valve 342 configured to control the suction between the suction source 320 and the endoscope 310A so that suction may be turned off during all or a portion of the application cycle of the irrigation fluid. The irrigation source 330 can be connected to the suction/irrigation control unit 340 via an external irrigation line 336. The pump included in the suction/irrigation control unit 340 can pressurize the irrigation fluid before entering the endoscope 310A via the irrigation line 336. As illustrated in FIG. 3A, the external suction line 326 and the external irrigation line 336 can be connected together at a common fitting 350, which can be coupled to a common line 356 for supplying the fluid or suction to the endoscope 310A via the irrigation/suction port 313.

The control module in the suction/irrigation control unit 340 may be configured to control the operation of the endoscope 310A in response to user commands from the user interface 341. In an example, the control module may detect clogging in a working channel (e.g., a unified irrigation/suction channel, a separate irrigation channel, or a separate suction channel) based on a flow rate sensed from the working channel, and unclog the obstructed channel such as by alternating application of irrigation fluid and suction pressure. The control module may automatically active and adjust one or more of irrigation flow parameters or one or more suction flow parameters to keep the pressure of the anatomical environment (the "environmental pressure") under control, such as to maintain the environmental pressure at substantially a user-specified pressure level, as discussed above with reference to FIG. 1.

The system 300B as illustrated in the FIG. 3B is similar to the system 300A, and comprises an endoscope 310B, a suction source 320, an irrigation source 330, and a control suction/irrigation control unit 340. Similar to the endoscope 310A, the endoscope 310B can include a tube 311, a hub 312, a light port 314, and a visual port 315. However, instead of a single irrigation/suction port 313, the endoscope 310B includes separate suction port 313A and irrigation port 313B, adapted to be in fluid communication with the suction source 320 and the irrigation source 330, respectively. The suction source 320 is fluidly coupled to the suction port 313A via the external suction line 326. The irrigation source 330 is fluidly coupled to the irrigation port 313B via the external irrigation line 336. The suction port 313A and the irrigation port 313B can each open to one or more working channels inside the tube 311. In an example, an irrigation channel and a suction channel are separately disposed within the tube 311. The suction port 313A can be selectively open to the suction channel or the irrigation channel. Similarly, the irrigation port 313B can be selectively open to the suction channel or the irrigation channel inside the tube 311.

Figure 5:
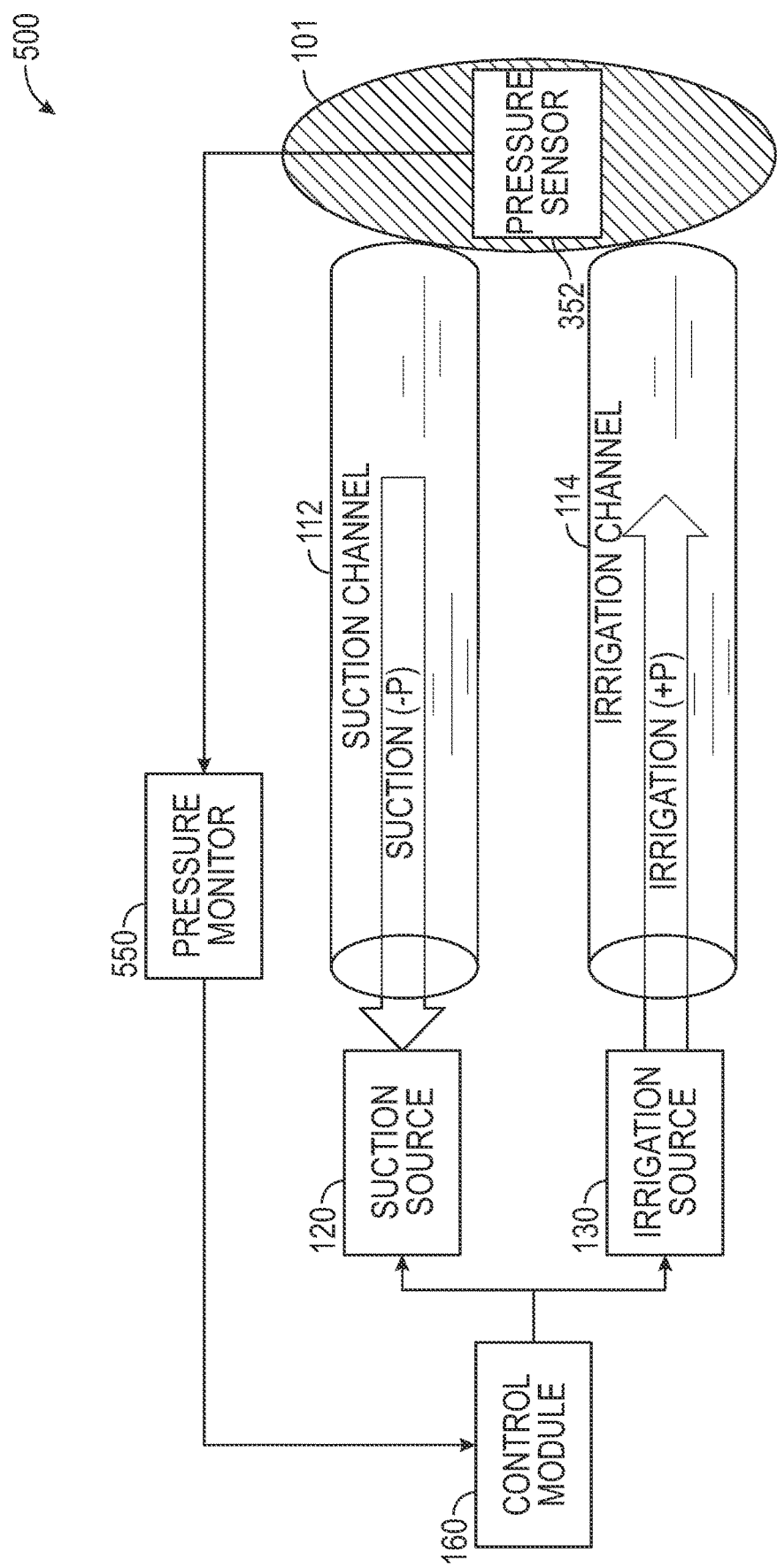
FIG. 5 is a diagram illustrating an exemplary feedback-controlled pressure regulation system that regulates the environmental pressure in the absence of channel clogging.

FIG. 5 is a diagram illustrating an exemplary feedback-controlled pressure regulation system 500, which is an embodiment of the environmental pressure control portion of the system 100. The system 500 can be configured to regulate the environmental pressure at the anatomical site when no channel clogging is indicated, and when the system 500 operates in the standard mode of irrigation/suction (e.g., controlling the suction source 120 to provide suction pressure to the suction channel 112, and controlling the irrigation source 130 to provide a flow of irrigation fluid to the irrigation channel 114). The system 500 can regulate the environmental pressure via automatic adjustment of suction and/or irrigation flow rates in the respective suction channel 112 and irrigation channel 114. In an example, a longitudinal axis of the suction channel 112 and a longitudinal axis of the irrigation channel 114 may be parallel to each other. In an example, the suction channel 112 and the irrigation channel 114 may be coaxially disposed with a common axis, such as in a nested configuration. In an example, irrigation and suction can be applied through the same working channel, such as a unified irrigation/suction channel, at different times. A pressure monitor 550 can monitor the pressure of the anatomical environment 101 via a pressure sensor 352. By way of example and not limitation, the control module 160 may include a Proportional-Integral (PI) controller, or a Proportional-Integral-Derivative (PID) controller, among other feedback controllers. The difference between the sensed pressure (at the pressure monitor 550) and the desired pressure, also referred as the "error", can be used to determine the P, I, or D terms in the feedback controller.

Depending on the desired pressure (or the desired flow condition) provided by a user, the system 500 may operate in a stable pressure mode when the desired pressure is substantially net-zero (corresponding to a desired flow condition of substantially equal inflow rate of irrigation fluid applied to the anatomical environment and outflow rate of suction applied to the anatomical environment), or a pressure control mode when the desired pressure is a positive pressure or a negative pressure (corresponding to a desired flow condition of an imbalance between the inflow rate and the outflow rate). When operating in the stable pressure mode, the irrigation flow rate or the suction flow rate can be manually adjusted by a user, such as via respective user controls on the user interface 140. During an endoscopic procedure, an increase in the irrigation flow rate may result in an increase in the environmental pressure at the anatomical site, which can be sensed by the pressure monitor 550. The control module 160 can responsively activate suction by applying suction pressure to the suction channel 112. Suction can produce a negative pressure to offset the increased pressure produced by the irrigation. The control module 160 can adjust the suction flow rate or the suction pressure until the pressure increase (due to the increased irrigation) is substantially neutralized by the suction flow. The environmental pressure can then be driven towards, and maintained at, substantially zero.

Likewise, an increase in the suction flow rate may result in a decrease in the environmental pressure at the anatomical site. The control module 160 can responsively activate irrigation by providing a flow of irrigation fluid to the irrigation channel 114. Irrigation can produce a positive pressure to offset the decreased pressure produced by the suction. The control module 160 can adjust the irrigation flow rate until the pressure drop (due to the increased suction) is substantially neutralized by the irrigation flow. The environment pressure can then be driven towards, and maintained at, substantially zero.

In certain circumstances, it is desirable to maintain a positive or a negative environmental pressure, at the anatomical site. A controlled positive pressure within a safety range can help distend an anatomy (e.g., ureters, kidney, uterus, or other organs) during the endoscopic procedure to allow for better visibility of the anatomy via the scope, without causing tissue damage due to excessive positive pressure. A positive pressure may also prevent tissue debris or stone fragments from getting stuck in the anatomy and assist in the removal of them from the anatomy. In some cases, maintaining a controlled negative pressure within a safety range during the endoscopic procedure can also facilitate debris extraction from the anatomy, without putting an internal organ at a risk of excessive negative pressure.

When a positive desired environmental pressure is provided by a user such as via the user interface 140, the system 500 may operate in a pressure control mode. The control module 160 can automatically increase the irrigation flow rate through the irrigation channel 114 to increase the positive environmental pressure at the anatomical site. Additionally or alternatively, the control module 160 can automatically decrease the suction flow rate through the suction channel 112 to reduce the negative pressure at the anatomical site. The automatic adjustments of irrigation and/or suction can be continued until the sensed environmental pressure reaches substantially a level of the desired positive pressure.

Likewise, the system 500 may operate in the pressure control mode when a negative desired environmental pressure is provided by the user such as via the user interface 140. The control module 160 can automatically increase the suction flow rate through the suction channel 112 to increase the negative environmental pressure at the anatomical site. Additionally or alternatively, the control module 160 can automatically decrease the irrigation flow rate through the irrigation channel 114 to reduce the positive pressure at the anatomical site. The automatic adjustments of irrigation and/or suction can be continued until the sensed environmental pressure reaches substantially a level of the desired negative pressure.

The control module 160 can include a safety mechanism to keep the pressure of the anatomical environment within a safety range defined by a lower bound of negative pressure and an upper bound of positive pressure. If the sensed environmental pressure reaches the upper bound of positive pressure, the control module 160 can automatically shut down, reduce, or maintain at present rate of irrigation flow to prevent further increase in the environmental pressure. Likewise, if the sensed environmental pressure reaches the lower bound of negative pressure, the control module 160 can automatically shut down, reduce, or maintain at present rate of suction flow to prevent further decrease in the environmental pressure. When the system operates in the pressure control mode, the desired positive pressure and the desired negative pressure received from a user are checked to ensure that they fall within the safety range. In a non-limiting example, the desired positive pressure is 5 pound-force per square inch (psi) (or approximately 34.5 kilopascal (kPa)), the desired negative pressure is –5 psi (or approximately –34.5 kPa), and the safety range is between a lower bound of –6 psi (or approximately 41.4 kPa) and an upper bound of 6 psi (or approximately 41.4 kPa). In an example, a warning can be issued (e.g., from the user interface 140) if the desired positive pressure received from a user exceeds the upper bound of positive pressure, or if desired negative pressure is lower than the safety bound of negative pressure. With such a safety mechanism, the control module 160 can maintain the environmental pressure at a user-specified level, while at the same time preventing or minimizing excess positive or negative pressures imposed on the anatomical environment during the procedure.

Figure 6A:
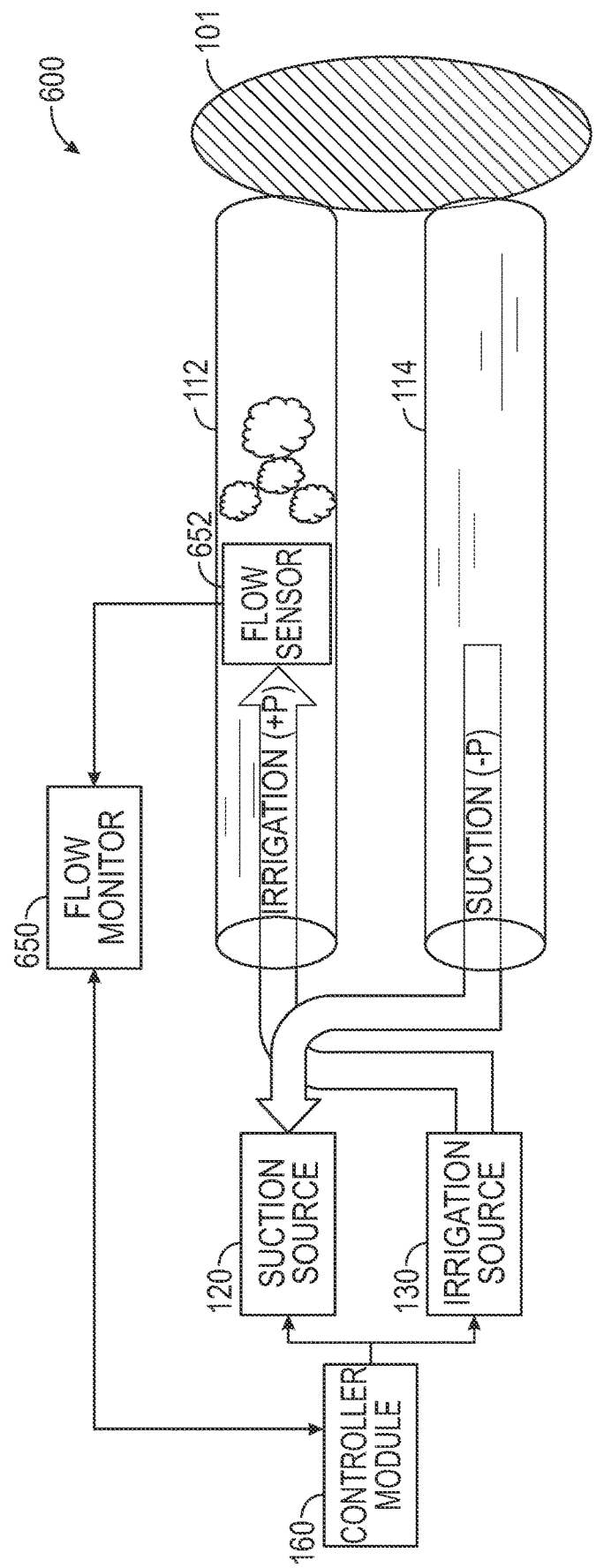
FIG. 6A is a diagram illustrating an exemplary feedback-controlled pressure regulation system that regulates the environmental pressure in the presence of clogging in a suction channel.

FIG. 6A is a diagram illustrating an exemplary feedback-controlled pressure regulation system 600, which is an embodiment of the system 100. The system 600 can be configured to regulate the pressure of the anatomical environment 101 (the "environmental pressure") in the presence of clogging in the suction channel 112. As discussed above with reference to FIG. 4A, when clogging in the suction channel 112 is detected, the clog controller 161 of the controller module 160 can switch from a standard mode of applying suction pressure to the suction channel 112 (see FIG. 5) to an unclogging mode where the irrigation source 130 is fluidly coupled to the suction channel 112 to provide an irrigation flow to the suction channel 112.

The irrigation flow applied to the suction channel 112 may result in an increase in the anatomical pressure at the anatomical site. The pressure controller 162 of the control module 160 can regulate the environmental pressure via automatic adjustment of suction and/or irrigation flow rates through the suction channel 112 and irrigation channel 114. For example, in response to the increase in the environmental pressure (such as sensed by the pressure monitor 550), the pressure controller 162 can automatically apply a suction pressure to the irrigation channel 114. If the irrigation channel 114 is not clogged, the applied suction in the irrigation channel 114 can produce a negative pressure on the anatomical environment 101 to offset the pressure increase produced by the irrigation through the suction channel 112. In an example, the pressure monitor 550 can continuously or periodically monitor the environmental pressure, and the pressure controller 162 can adjust the suction flow rate, or the suction pressure, to drive the environmental pressure towards a level of a desired pressure.

In an example, the desired pressure is a substantially net-zero pressure. The pressure controller 162 can adjust the suction flow rate or suction pressure in the irrigation channel 114 to substantially neutralize the increase in the sensed environmental pressure. As such, the environmental pressure can be driven towards, and maintained at, substantially zero. In another example, the desired pressure is a positive pressure. The pressure controller 162 can adjust the suction flow rate or suction pressure in the irrigation channel 114 at a level that drives the sensed environmental pressure towards a level of the desired positive pressure. An example of the desired positive pressure is 5 pound-force per square inch (psi), or approximately 34.5 kPa. In yet another example, the desired pressure is a negative pressure, and the pressure controller 162 can adjust the suction flow rate or suction pressure in the irrigation channel 114 at a level that drives the sensed environmental pressure towards a level of the desired negative pressure. An example of the desired negative pressure is –5 psi, or equivalently approximately –34.5 kPa.

Figure 6B:
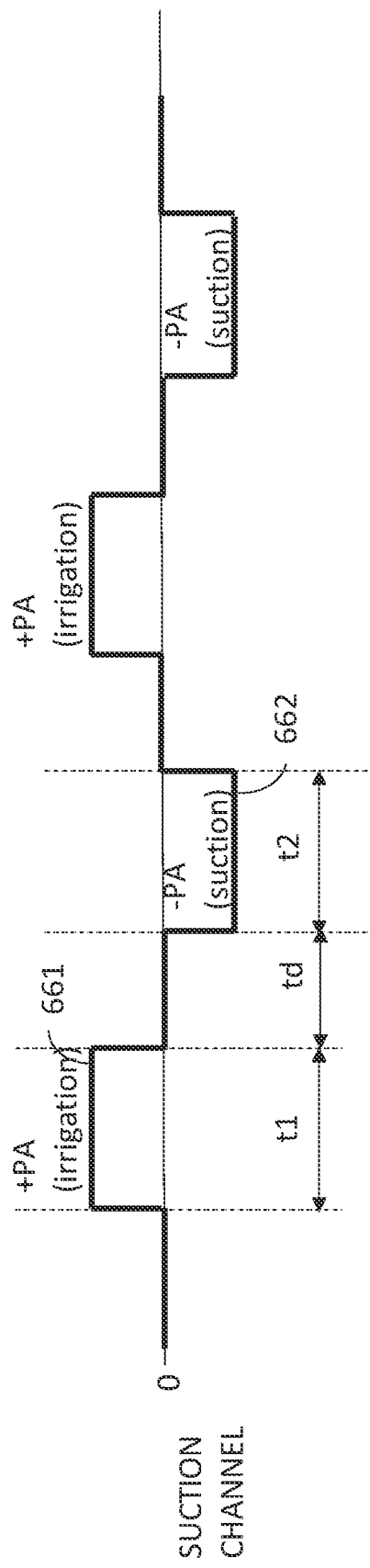
FIG. 6B is a timing diagram of activating irrigation/suction in the suction channel during unclogging of an obstructed suction channel.
Figure 7A:
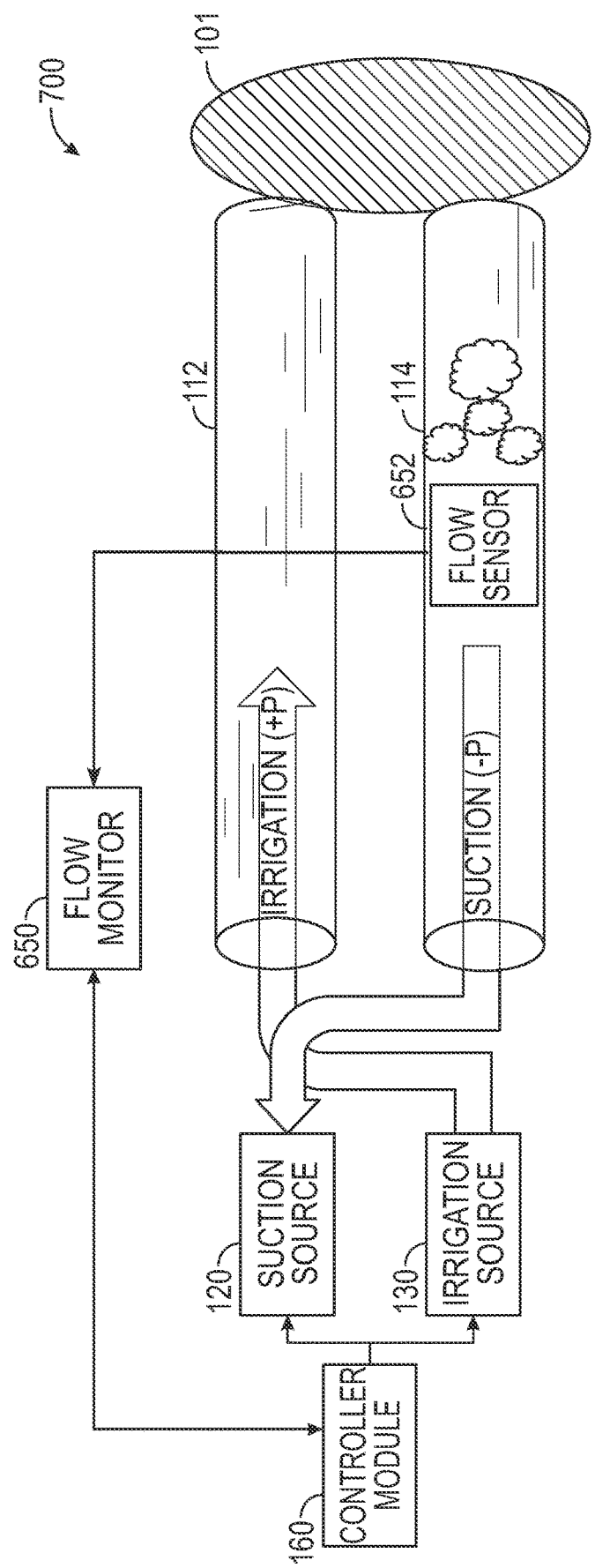
FIG. 7A is a diagram illustrating an exemplary feedback-controlled pressure regulation system that regulates the environmental pressure in the presence of clogging in an irrigation channel.

As discussed above with reference to FIGS. 3A-3B, unclogging may involve alternating between the applications of suction and irrigation to the obstructed channel. FIG. 6B is a timing diagram of activating irrigation/suction in the suction channel when clogging occurs in the suction channel 112 (as illustrated in FIG. 7A). To unclog the suction channel, irrigation is applied to the suction channel for a duration t1 (the "irrigation duration"). After a transition period $t_d$, suction pressure is applied to the suction channel for a duration t2 (the "suction duration"). The transition period $t_d$ allows clog particles of different sizes and masses to travel for different distances along the suction channel, which facilitates particle separation and channel unclogging. Irrigation may cause a positive anatomical pressure (+PA) 661, and suction may cause a negative pressure (–PA) 662 at the anatomical site.

Figure 6C:
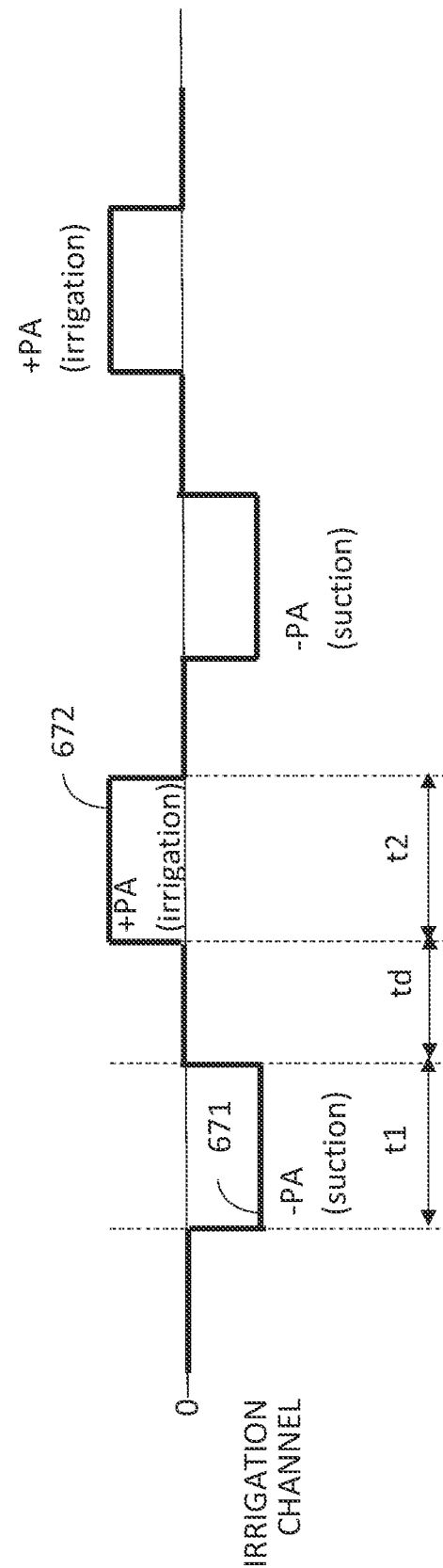
FIG. 6C is a timing diagram of activating irrigation/suction in the irrigation channel to maintain a desired pressure at the anatomical site during unclogging of an obstructed suction channel.

FIG. 6C is a timing diagram of activating irrigation/suction in the irrigation channel to achieve pressure control at the anatomical site, such as to maintain a desired anatomical pressure during the unclogging process. During t1, the pressure controller 162 can activate suction to the irrigation channel 114, which can produce a negative anatomical pressure (–PA) 671 to offset the positive anatomical pressure (+PA) 661 at the anatomical site. During t2, the pressure controller 162 can activate irrigation to the irrigation channel 114, which can produce a positive anatomical pressure (+PA) 672 to offset the negative anatomical pressure (–PA) 662 at the anatomical site. As such, the pressure of the anatomical environment can be maintained at a desired level while the obstructed suction channel is being unclogged.

When the flow monitor 650 senses an increase in flow rate through the suction channel 112 via a flow sensor 652, the obstructed channel is determined to be successfully unclogged. The clog controller 161 can switch back to the standard mode of irrigation/suction operation (e.g., controlling the suction source to apply suction pressure to the suction channel, and controlling the irrigation source to provide irrigation fluid to the irrigation channel). The pressure controller 162 can operate the suction and irrigation to keep the environmental pressure under control, as discussed above with reference to FIG. 5.

FIG. 7A is a diagram illustrating an exemplary feedback-controlled pressure regulation system 700, which is an embodiment of the system 100. The system 700 can be configured to regulate the pressure imposed on the anatomical environment 101 (the "environmental pressure") in the presence of clogging in the irrigation channel 114. As discussed above with reference to FIG. 4A, when clogging in the irrigation channel 112 is detected, the clog controller 161 of the controller module 160 can switch from a standard mode of providing irrigation fluid to the irrigation channel 114 to an unclogging mode where the suction source 120 can be fluidly coupled to the irrigation channel 114 to suck or vacuum the obstructed irrigation channel 114.

The suction pressure applied to the irrigation channel 114 may result in a decrease in the pressure at the anatomical site of the anatomical environment 101. The pressure controller 162 of the control module 160 can regulate the environmental pressure via automatic adjustment of suction and/or irrigation flow rates through the suction channel 112 and irrigation channel 114. For example, in response to the decrease in the environmental pressure (which can be sensed by the pressure monitor 550), the pressure controller 162 can automatically activate irrigation fluid flow into the suction channel 112. If the suction channel 112 is not clogged, the applied irrigation fluid in the suction channel 112 can produce a positive pressure to offset the pressure decrease at the anatomical environment 101 produced by the suction through the irrigation channel 114. In an example, the pressure monitor 550 can continuously or periodically monitor the environmental pressure, and the pressure controller 162 can adjust the irrigation flow rate to drive the environmental pressure towards a level of a desired pressure.

In an example, the desired pressure is a substantially net-zero pressure. The pressure controller 162 can adjust the irrigation flow rate through the suction channel 112 at a level that substantially neutralizes the decrease in the sensed environmental pressure. The environmental pressure, as sensed by the pressure monitor 550, can then be driven towards, or maintained at, substantially zero. In another example, the desired pressure is a positive pressure. The pressure controller 162 can adjust the irrigation flow rate through the suction channel 112 at a level that drives the sensed environmental pressure towards a level of the desired positive pressure. In yet another example, the desired pressure is a negative pressure, and the pressure controller 162 can adjust the irrigation flow rate through the suction channel 112 at a level that drives the sensed environmental pressure towards a level of the desired negative pressure.

FIG. 7B is a timing diagram of activating irrigation/suction in the irrigation channel when clogging occurs in the irrigation channel 114 (as illustrated in FIG. 7A). To unclog the irrigation channel, suction is applied to the irrigation channel for a duration t3 (the "suction duration"). After a transition period $t_d$, irrigation pressure is applied to the irrigation channel for a duration t4 (the "irrigation duration"). The transition period $t_d$ allows clog particles of different sizes and masses to travel for different distances along the irrigation channel, which facilitates particle separation and channel unclogging. Suction may cause a negative anatomical pressure (−PA) 761, and irrigation may cause a positive anatomical pressure (+PA) 762, at the anatomical site.

FIG. 7C is a timing diagram of activating irrigation/suction in the suction channel to achieve pressure control at the anatomical site, such as to maintain a desired anatomical pressure during the unclogging process. During t3, the pressure controller 162 can activate irrigation to the suction channel 112, which produces a positive anatomical pressure (+PA) 771 to offset the negative anatomical pressure (−PA) 761 at the anatomical site. During t4, the pressure controller 162 can activate suction to the suction channel 112, which produces a negative anatomical pressure (−PA) 772 to offset the positive anatomical pressure (+PA) 762 at the anatomical site. As such, the pressure of the anatomical environment can be maintained at a desired level while the obstructed irrigation channel is being unclogged.

When the flow monitor 650 senses an increase in flow rate through the suction channel 112 via a flow sensor 652, the obstructed channel is determined to be successfully unclogged. The clog controller 161 can switch back to the standard mode of irrigation/suction operation (e.g., controlling the suction source to apply suction pressure to the suction channel, and controlling the irrigation source to provide irrigation fluid to the irrigation channel). The pressure controller 162 can operate the suction and irrigation to keep the environmental pressure under control, as discussed above with reference to FIG. 5.

Figure 8:
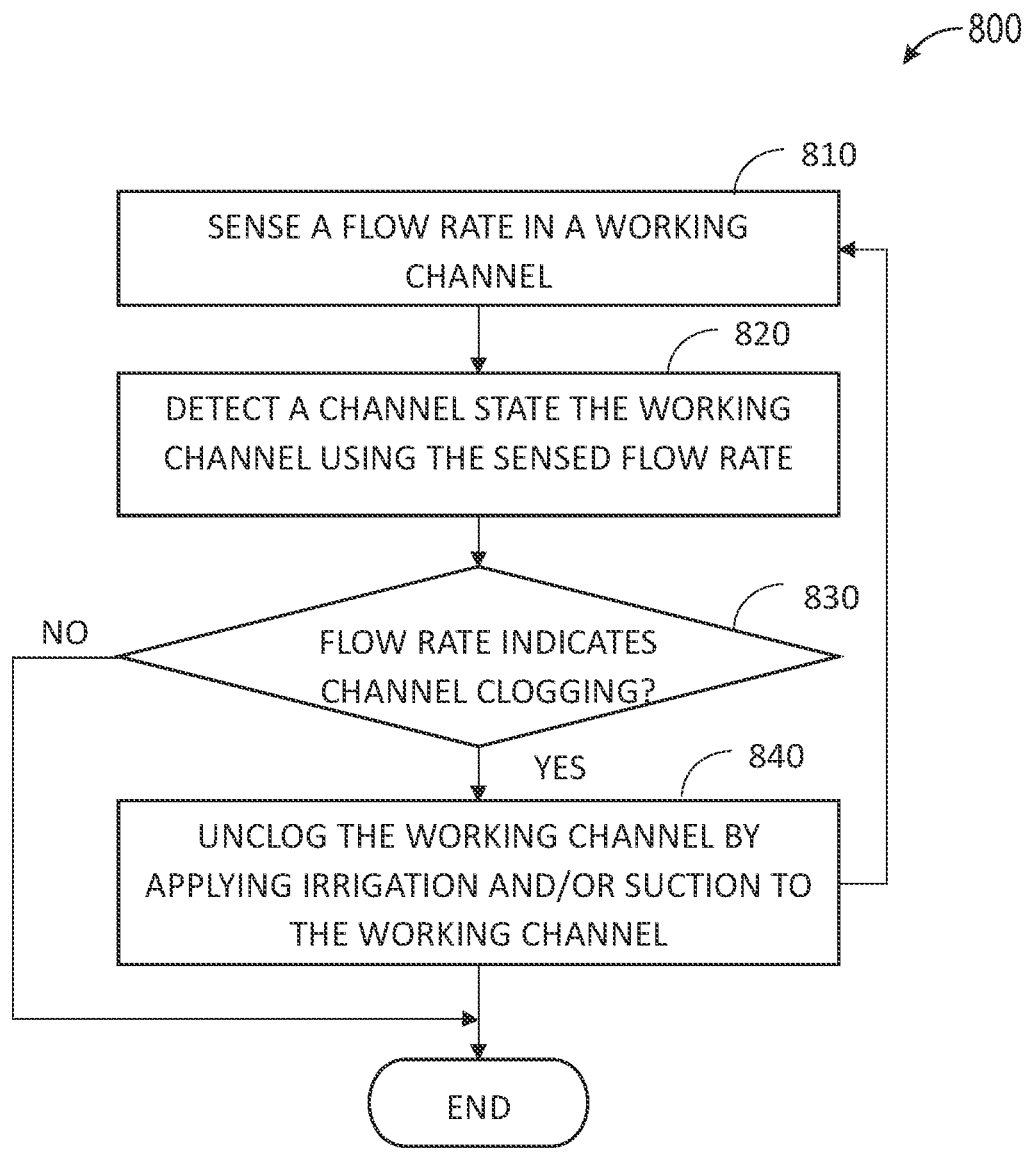
FIG. 8 is a flow chart illustrating a method for in situ unclogging a working channel in a medical device during a minimally invasive procedure.

FIG. 8 is a flow chart illustrating a method 800 for in situ unclogging a working channel in a medical device during a minimally invasive procedure, such as an endoscopic procedure. The medical device includes a tubular portion insertable into the interior of a hollow organ or a cavity of the body to assist in medical diagnosis or surgical treatment. Examples of the medical device can include a tissue removal device such as illustrated in FIG. 2A-2B, or an endoscope such as illustrated in FIGS. 3A-3B, among others. The medical device can comprise one or more working channels configured to provide irrigation fluid to the anatomical site, and to transport the tissue debris, calculi or mass, body fluid, and irrigation fluid, referred to herein collectively as unwanted matters, away from the anatomical site. The working channel can be at least partially located inside the tubular portion of the medical device. In an example, the working channel is a unified irrigation/suction channel controllably used for irrigation and suction (e.g., at different times). In another example, the working channels can include separate irrigation channel and suction channel disposed within the tubular portion of the medical device. The irrigation channel and the suction channel may each receive irrigation fluid or suction pressure, such as under automatic control by a controller unit to perform different tasks or to fulfill different functions during an endoscopic procedure in accordance with various embodiments discussed in this document.

The method 800 comprises one or more processes of operating an unclogging system, such as the system 100 or variant thereof, such as one of the systems 200, 300A, or 300B. Although the processes of the method 800 are drawn in one flow chart, they are not required to be performed in a particular order. In various examples, some of the processes can be performed in a different order than that illustrated herein.

At 810, a flow rate through a working channel can be sensed using a flow sensor, which can be positioned inside the working channel of the medical device. Examples of the flow sensor can include thermal anemometers that measure a transfer rate of heat generated from a heat source, differential pressure sensors that measure pressure drop over a range of locations, ultrasonic flow sensors that measures the Doppler effect of frequency shift or time-of-travel/flight, electromagnetic sensors that measure a change in fluid conductance indicative of flow rate, among others. At 820, a channel state indicating a presence of an absence of clogging in the working channel can be detected based on the sensed flow rate, such as using the clog controller 161. In an example, a channel clogging can be detected in response to a decrease in flow rate, such as below a first flow rate threshold. An absence of clogging, or a successful unclogging of an obstructed working channel, can be detected if the sensed flow rate increases and exceeds a second flow rate threshold. In an example, the first or second flow rate threshold can each be relative to (e.g., a specific percentage of) a reference flow rate, such as that measured in the unclogged channel.

If at 830 the sensed flow rate indicates a presence of clogging in a working channel, then at 840 an unclogging mode of irrigation/suction operation is activated to unclog the obstructed working channel. When separate irrigation channel and suction channel are used in the medical device, the unclogging mode includes an application of a flow of irrigation fluid to the suction channel, and/or an application of suction pressure to the irrigation channel. This is different from a standard mode of irrigation/suction operation where the suction source provides suction pressure to the suction channel, and the irrigation source provides a flow of irrigation fluid to the irrigation channel. In an example, the unclogging mode at 840 can include alternating between irrigation and suction to the obstructed channel. As discussed above with reference to FIG. 4A, the clog controller 161 can controllably activate a suction source (e.g., the suction source 120) to provide suction pressure to the obstructed working channel for a specified suction duration (as illustrated in panel 420 of FIG. 4A). The clog controller 161 can alternatively or additionally activate an irrigation source (e.g., the irrigation source 140) to apply a flow of irrigation fluid to the obstructed working channel for a specified irrigation duration (as illustrated in panel 440 of FIG. 4A). The suction pressure, the suction flow rate, the irrigation flow rate, or the pump pressure to pressurize the irrigation fluid can be adjusted by a user.

Clog particles of different sizes (thus different masses) may respond differently to the suction or to the flushing irrigation fluid. As illustrated in FIG. 4A, suction, irrigation, or alternating between the suction and irrigation can assist in dislodging smaller particles from the clog mass and separating from the rest of the clog, because smaller particles can move along the direction of suction flow or the direction of fluid flow at a faster speed and travel for a longer distance than larger particles. The separated particles can be more easily and efficiently extracted down the working channel by applying additional suction or irrigation flow thereto. In an example, one or more of the suction pressure, the suction flow rate, the irrigation flow rate, or the pump pressure can be varied to separate out particles by size. For example, a higher flow rate can be applied to remove larger particles, and a lower flow rate can be applied to remove smaller particles through the channel.

The flow rate can be continuously or periodically monitored 810 during the unclogging process. When the monitored flow rate increases and exceeds a threshold at 830, the obstructed channel is deemed unclogged successfully. The unclogging mode of operation can then be switched back to the standard mode of irrigation/suction operation.

Figure 9:
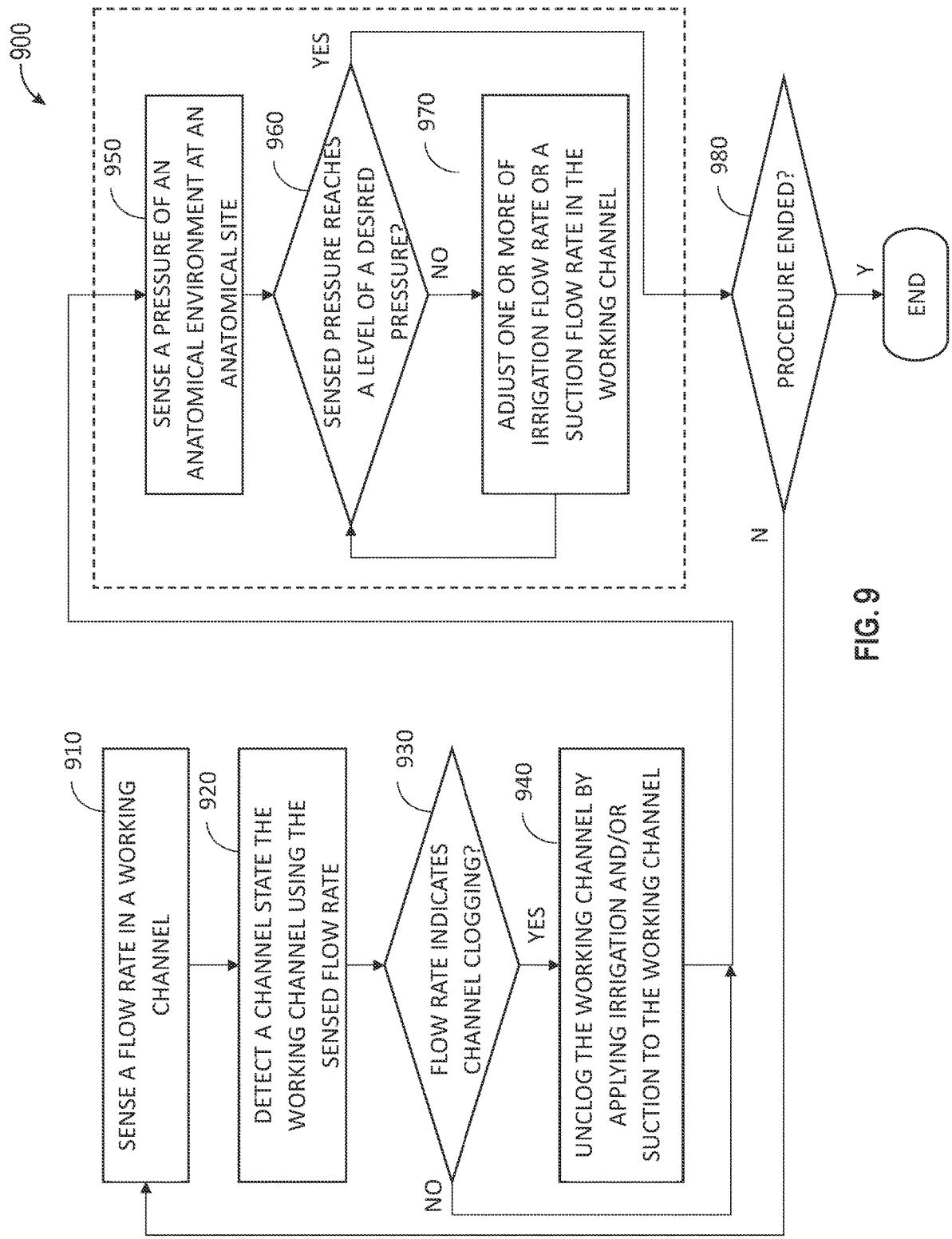
FIG. 9 is a flow chart illustrating a method for in situ unclogging a working channel of a medical device and maintaining the pressure of an anatomical environment at the anatomical site at substantially a desired level.

FIG. 9 is a flow chart illustrating a method 900 for in situ unclogging a working channel of a medical device, while keeping the pressure of the anatomical environment (the "environmental pressure") under control, such as maintaining the environmental pressure at substantially a user-specified pressure level. The process of controlling the environmental pressure can be implemented in and executed by a pressure controller, such as the pressure controller 162. The processes of the method 900 are not required to be performed in a particular order. For example, some steps can be performed in a different order than that illustrated herein.

The method 900 includes steps 910 through 940 for detecting clogging in a working channel and unclogging said obstructed channel, which are similar to the steps 810 through 840 of method 800. The method 900 further includes steps 950 through 980 to regulate the environmental pressure during the procedure (e.g., an endoscopic procedure) in the presence, or in the absence, of channel occlusion. As stated previously, suction may result in a negative pressure change at the anatomical site, while irrigation may result in a positive pressure change at the anatomical site. Negative and positive pressure changes may pose adverse effect on internal organs exposed to the anatomical site. Maintaining the environmental pressure at a controlled pressure level can increase patient safety and effectively reduce procedure time.

Regulation of the environmental pressure can be achieved via automatic adjustment of suction and/or irrigation flow rates in one or more working channels. Specifically, at 950, the environmental pressure can be sensed using a pressure sensor. The pressure sensor may be attached to or integrated into a distal portion of the medical device, such that the sensor is in contact with the anatomical environment. Examples of the pressure sensor can include resistive, capacitive, piezoelectric, optical, or Micro Electro-Mechanical System (MEMS) pressure sensors.

At 960, the sensed tissue present can be compared to a desired pressure, such as provided by a user via the user interface 140. The desired pressure represents a pressure to be maintained at the anatomical environment during the procedure. In one example, the desired pressure is a substantially net-zero pressure. In another example, the desired pressure is a positive pressure. In yet another example, the desired pressure is a negative pressure. Maintaining a controlled positive pressure within a safety range can help distend an anatomy (e.g., ureters, kidney, or other organs) during the endoscopic procedure to allow for better visibility of the anatomy via the scope, without causing tissue damage due to excessive positive pressure. A positive pressure may also prevent tissue debris or stone fragments from getting stuck in the anatomy, and assist in the removal of them from the anatomy. In some cases, maintaining a controlled negative pressure within a safety range during the endoscopic procedure can also facilitate debris extraction from the anatomy, without putting an internal organ at a risk of excessive negative pressure.

If at 960 the sensed pressure does not reach substantially a level of the desired pressure (that is, within a range of tolerance, such as ±5-10% of the desired pressure), then at 970 one or more of an irrigation flow rate or a suction flow rate through one or more working channels can be adjusted, such as using the pressure controller 162, to drive the environmental pressure towards a level of the desired pressure. In some examples, in addition to or in lieu of a desired pressure level, a desired flow condition can be received, such as from the user interface 140. The desired flow condition includes information about inflow (e.g., a flow rate of irrigation fluid applied to the anatomical environment) relative to outflow (e.g., a flow rate of suction applied to the anatomical environment), and corresponds to the desired pressure to be applied to the anatomical environment. One or more of an irrigation flow rate or a suction flow rate through one or more working channels can be varied to maintain the desired flow condition during the procedure.

The pressure control process at 970 can be carried out via a standard mode of irrigation/suction operation, when no clogging is detected in any working channel, or the obstructed channel has been successfully unclogged. As described above with reference to FIG. 5, suction applied to the suction channel can produce a negative pressure of the anatomical environment, which can offset an increase in environmental pressure produced by an increased irrigation flow rate. The suction flow rate, or the suction pressure, can be adjusted until the increase in the sensed pressure (such as caused by the increased irrigation) is substantially neutralized by the suction flow, thereby resulting in a desired substantially net-zero pressure; or until the sensed environmental pressure reaches substantially a level of the desired positive pressure or the desired negative pressure. Similarly, a flow of irrigation fluid provided to the irrigation channel can produce a positive pressure of the anatomical environment, which can offset a decrease in environmental pressure produced by suction. The irrigation flow rate can be adjusted until the decrease in the sensed pressure (such as caused by the increased suction) is substantially neutralized by the irrigation flow, thereby resulting in a desired substantially net-zero pressure; or until the sensed environmental pressure reaches substantially a level of the desired positive pressure or the desired negative pressure.

The pressure control process at 970 can be carried out via an unclogging mode of irrigation/suction operation, when at least one, but not all, of the working channels are clogged. FIG. 6A illustrates an example where the suction channel is clogged and the irrigation channel is not clogged. As discussed therein, a flow of irrigation fluid can be applied to the suction channel to unclog the obstructed suction channel. This may produce an increase in the environmental pressure, as can be detected by a pressure sensor. Suction pressure may be applied to the irrigation channel, which may produce a negative pressure to offset the pressure increase at the anatomical environment. The suction flow rate, or the suction pressure, in the irrigation channel can be adjusted until the increase in the sensed pressure (resulted from the increased irrigation in the obstructed suction channel) is substantially neutralized by the suction flow, thereby resulting in a desired substantially net-zero pressure; or until the sensed environmental pressure reaches substantially a level of the desired positive pressure or the desired negative pressure.

In another example where the irrigation channel is clogged and the suction channel is not clogged, suction pressure may be applied to the irrigation channel to unclog the obstructed irrigation channel. This may produce a decrease in the environmental pressure. As discussed above with reference to FIG. 7A, a flow of irrigation fluid may be applied to the suction channel, which may produce a positive pressure to offset the negative increase at the anatomical environment. The irrigation flow rate can be adjusted until the decrease in the sensed pressure (resulted from the increased suction in the obstructed irrigation channel) is substantially neutralized by the irrigation flow, thereby resulting in a desired substantially net-zero pressure; or until the sensed environmental pressure reaches substantially a level of the desired positive pressure or the desired negative pressure.

At 980, the procedure is checked for completion. If the procedure is not completed, then the flow rate sensing and declogging processes 910 through 940, and the pressure control processes 950 through 980, may be continued.

The controlled irrigation and suction, including alternating between the application of irrigation fluid and application of suction pressure to the same clogged channel, as described in methods 800 and 900, can effectively unclog the channel by separating the fragments of different sizes that accumulate to clog the channel. The pressure control via the application of irrigation and/or suction in one or more working channels, as described in method 900, can effectively avoid or minimize the excess positive or negative pressures imposed on the internal organ during an endoscopic procedure, in the presence of, and in the absence of, channel clogging. As a result, overall procedure time can be reduced and patient safety can be improved.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for unclogging at least one working channel of a medical device during a medical procedure at an anatomical site, the system comprising:
    an irrigation system including an irrigation source and a suction source each configured to be operably fluidly coupled to the at least one working channel; and
    a controller circuit configured to, in a presence of clogging in the at least one working channel:
    fluidly couple the irrigation source and the suction source to the at least one working channel at respective times; and
    alternate between an irrigation through the at least one working channel via the irrigation source for a first time period and an aspiration through the at least one working channel via the suction source for a second time period to unclog the at least one working channel, the irrigation and the aspiration separated by a transition period during which the irrigation and the aspiration are withheld to allow clogging-causing particles of different sizes or masses to travel for different distances in the at least one working channel so as to spatially separate from each other.

2. The system of claim 1,
    wherein the irrigation source is configured to supply irrigation fluid at an adjustable irrigation flow rate when fluidly coupled to the at least one working channel,
    wherein the suction source is configured to apply suction pressure at an adjustable suction flow when fluidly coupled to the at least one working channel.

3. The system of claim 1, wherein the transition period has a predetermined duration.

4. The system of claim 1, comprising a flow sensor configured to sense a flow rate of fluid in the at least one working channel,
    wherein the controller circuit is configured to detect the presence of clogging in the at least one working channel based on the sensed flow rate.

5. The system of claim 1, wherein the at least one working channel includes a suction channel and an irrigation channel,
    wherein the controller circuit is configured to:
    fluidly couple the irrigation source to one of the suction channel or the irrigation channel to supply irrigation fluid thereto; and
    fluidly couple the suction source to the other of the suction channel or the irrigation channel to apply suction pressure thereto.

6. The system of claim 5, wherein the controller circuit is configured to, in the presence of clogging in the suction channel, unclog the suction channel by performing one or more iterations including:
    fluidly coupling the irrigation source to the suction channel and supply the irrigation fluid thereto for the first time period;
    withholding the irrigation during the transition period; and
    subsequent to the withholding the irrigation, decoupling the irrigation source from the suction channel, and fluidly coupling the suction source to the suction channel and apply the suction pressure thereto for the second time period.

7. The system of claim 5, wherein the controller circuit is configured to, in the presence of clogging in the irrigation channel, unclog the irrigation channel by performing one or more iterations including:
    fluidly coupling the suction source to the irrigation channel and apply the suction pressure thereto for the first time period;
    withholding the irrigation during the transition period; and
    subsequent to the withholding the irrigation, decoupling the suction source from the irrigation channel, and fluidly coupling the irrigation source to the irrigation channel and supply the irrigation fluid thereto for the second time period.

8. The system of claim 5, further comprising a pressure sensor configured to sense a pressure of the anatomical site,
    wherein the controller circuit is configured to adjust one or more of an irrigation flow rate of the irrigation source or a suction flow rate of the suction source through the at least one working channel, such that the sensed pressure of the anatomical site is maintained at substantially a target pressure during the medical procedure.

9. The system of claim 8, further comprising a user interface configured to receive a user input of the target pressure to be maintained at the anatomical site during the medical procedure.

10. The system of claim 8, wherein the controller circuit is configured to, in the presence of clogging in the suction channel and during the unclogging thereof, alternate between the aspiration via the suction source and the irrigation via the irrigation source of the irrigation channel to maintain the sensed pressure of the anatomical site at substantially the target pressure.

11. The system of claim 8, wherein the controller circuit is configured to, in the presence of clogging in the irrigation channel and during the unclogging thereof, alternate between the irrigation via the irrigation source and the aspiration via the suction source of the suction channel to maintain the sensed pressure of the anatomical site at substantially the target pressure.

12. The system of claim 5, further comprising a flow sensor configured to sense a flow rate of fluid in at least one of the suction channel or the irrigation channel,
    wherein the controller circuit is configured to adjust one or more of an irrigation flow rate of the irrigation source or a suction flow rate of the suction source such that the sensed flow rate in the at least one working channel is maintained at substantially a target flow condition during the medical procedure.

13. A method of unclogging at least one working channel of a medical device during a medical procedure at an anatomical site using an irrigation system comprising an irrigation source and a suction source operably fluidly coupled to the at least one working channel, the method comprising:
    receiving channel state information indicating a presence or an absence of clogging in the at least one working channel during the procedure; and in a presence of clogging in the at least one working channel, via a controller circuit: fluidly coupling the irrigation source and suction source to the at least one working channel at respective times; and alternating between an irrigation through the at least one working channel via the irrigation source for a first time period and an aspiration through the at least one working channel via the suction source for a second time period to unclog the at least one working channel, the irrigation and the aspiration separated by a transition period during which the irrigation and aspiration are withheld to allow clogging-causing particles of different sizes or masses to travel for different distances in the at least one working channel so as to spatially separate from each other.

14. The method of claim 13, wherein alternating between the irrigation and the aspiration to unclog the at least one working channel includes:
supplying irrigation fluid at an adjustable irrigation flow rate when the irrigation source is fluidly coupled to the at least one working channel; and
applying suction pressure at an adjustable suction flow when the suction source is fluidly coupled to the at least one working channel.

15. The method of claim 13, further comprising:
sensing a flow rate of fluid in the at least one working channel using a flow sensor; and
detecting the presence of clogging in the at least one working channel based on the sensed flow rate.

16. The method of claim 13, wherein the at least one working channel includes a suction channel and an irrigation channel,
wherein fluidly coupling the irrigation source and suction source to the at least one working channel in the presence of clogging in the at least one working channel includes, via the controller circuit:
fluidly coupling the irrigation source to one of the suction channel or the irrigation channel to supply an irrigation fluid thereto at an adjustable irrigation flow rate; and
fluidly coupling the suction source to the other of the suction channel or the irrigation channel to apply suction pressure thereto at an adjustable suction flow rate.

17. The method of claim 16, wherein alternating between the irrigation and the aspiration to unclog the at least one working channel includes, in the presence of clogging in the suction channel, performing one or more iterations including:
fluidly coupling the irrigation source to the suction channel and supply the irrigation fluid thereto for the first time period;
withholding the irrigation during the transition period; and
subsequent to the withholding the irrigation, decoupling the irrigation source from the suction channel, and fluidly coupling the suction source to the suction channel and apply the suction pressure thereto for the second time period.

18. The method of claim 16, wherein alternating between the irrigation and the aspiration to unclog the at least one working channel includes, in the presence of clogging in the irrigation channel, performing one or more iterations including:
fluidly coupling the suction source to the irrigation channel and apply the suction pressure thereto for the first time period;
withholding the irrigation during the transition period; and
subsequent to the withholding the irrigation, decoupling the suction source from the irrigation channel, and fluidly coupling the irrigation source to the irrigation channel and supply the irrigation fluid thereto for the second time period.

19. The method of claim 16, further comprising:
sensing a pressure at the anatomical site using a pressure sensor, and
adjusting, via the controller circuit, one or more of the irrigation flow rate of the irrigation source or the suction flow rate of the suction source through the at least one working channel, such that the sensed pressure of the anatomical site is maintained at substantially a target pressure during the medical procedure.

20. The method of claim 16, further comprising:
sensing a flow rate of fluid in at least one of the suction channel or the irrigation channel; and
adjusting, via the controller circuit, one or more of the irrigation flow rate of the irrigation source or the suction flow rate of the suction source such that the sensed flow rate in the at least one working channel is maintained at substantially a target flow condition during the medical procedure.

* * * * *

UNITED STATES PATENT AND TRADEMARK OFFICE
CERTIFICATE OF CORRECTION

| | | |
|---|---|---|
| PATENT NO. | : 12,414,820 B2 | Page 1 of 1 |
| APPLICATION NO. | : 18/611831 | |
| DATED | : September 16, 2025 | |
| INVENTOR(S) | : Shelton et al. | |

It is certified that error appears in the above-identified patent and that said Letters Patent is hereby corrected as shown below:

In the Claims

In Column 34, Line 30, in Claim 19, delete "sensor," and insert --sensor;-- therefor Signed and Sealed this
Twenty-eighth Day of October, 2025

John A. Squires
*Director of the United States Patent and Trademark Office*